US007854352B2

(12) United States Patent
Davies et al.

(10) Patent No.: US 7,854,352 B2
(45) Date of Patent: Dec. 21, 2010

(54) FLUID DISPENSING DEVICE WITH STOPPER

(75) Inventors: Michael Birsha Davies, Ware (GB); James William Godfrey, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1330 days.

(21) Appl. No.: 10/548,716

(22) PCT Filed: Mar. 11, 2004

(86) PCT No.: PCT/GB2004/001002

§ 371 (c)(1), (2), (4) Date: Sep. 8, 2005

(87) PCT Pub. No.: WO2004/080606

PCT Pub. Date: Sep. 23, 2004

(65) Prior Publication Data

US 2006/0191959 A1 Aug. 31, 2006

(30) Foreign Application Priority Data

Mar. 11, 2003 (GB) ................................ 0305583.7

(51) Int. Cl.
*B67D 7/84* (2010.01)
*A61M 11/00* (2006.01)
*B65D 53/00* (2006.01)

(52) U.S. Cl. .................. 222/162; 222/183; 222/402.15; 128/200.23; 128/203.14; 215/344; 215/351; 215/235; 220/839; 604/19

(58) Field of Classification Search ................. 222/160, 222/162, 402.15, 183; 215/344, 341, 350, 215/351, 235; 220/839, 837; 604/19, 412, 604/414; 128/200.23, 203.14, 206.11, 200.14, 128/200.22, 207.18
See application file for complete search history.

(56) References Cited

U.S. PATENT DOCUMENTS 2,249,832 A * 7/1941 Hubschman ................ 222/420
3,446,403 A * 5/1969 Serio et al. .................. 222/158
3,462,034 A * 8/1969 Friedberg ................... 215/329
3,986,627 A * 10/1976 Zapp .......................... 215/237
4,714,200 A 12/1987 Sayama
4,771,769 A 9/1988 Hegemann et al.

(Continued)

FOREIGN PATENT DOCUMENTS

EP 0845299 A2 6/1998

(Continued)

*Primary Examiner*—Kevin P Shaver
*Assistant Examiner*—Stephanie E Williams
(74) *Attorney, Agent, or Firm*—James P. Riek

(57) ABSTRACT

A fluid dispensing device is disclosed having a body housing a pump action fluid discharge device having a dispensing nozzle. The fluid dispensing device comprises a body defining a cavity and a dispensing nozzle having a dispensing orifice, a fluid discharging device housed in the cavity, the fluid discharging device having a hollow casing defining a reservoir for containing a volume of fluid and a plunger slidingly engaged within the hollow casing, the plunger having a tubular portion which extends from a first end of the hollow casing for co-operation with the dispensing nozzle to enable pumped delivery of fluid from the reservoir to the dispensing nozzle, wherein the dispensing orifice of the dispensing nozzle is provided with a reversible stopper.

17 Claims, 17 Drawing Sheets

U.S. PATENT DOCUMENTS

| | | | | |
|---|---|---|---|---|
| 4,793,527 | A | | 12/1988 | Di Stefano et al. |
| 4,921,142 | A | | 5/1990 | Graf et al. |
| 4,944,429 | A | | 7/1990 | Bishop et al. |
| 4,946,069 | A | | 8/1990 | Fuchs |
| 5,143,236 | A | * | 9/1992 | Gueret ....................... 215/311 |
| 5,464,122 | A | * | 11/1995 | Lifshey ....................... 222/83 |
| 5,487,489 | A | | 1/1996 | Weiss et al. |
| 5,709,325 | A | | 1/1998 | Renault et al. |
| 6,055,979 | A | * | 5/2000 | Fuchs .................... 128/203.15 |
| 6,189,739 | B1 | | 2/2001 | von Schuckmann |
| 6,343,365 | B1 | | 1/2002 | Matsuzawa et al. |
| 6,454,477 | B1 | | 9/2002 | Sugiyama |
| 2004/0182814 | A1 | | 9/2004 | Suffa |
| 2005/0072861 | A1 | | 4/2005 | Petit |

FOREIGN PATENT DOCUMENTS

| | | | | |
|---|---|---|---|---|
| EP | 1 281 443 | A | | 2/2003 |
| EP | 1331036 | A1 | | 7/2003 |
| GB | 173123 | | | 12/1921 |
| GB | 2262137 | | * | 6/1993 |
| JP | 9225363 | | | 9/1997 |
| JP | 9313998 | | | 12/1997 |
| JP | 10001155 | | | 1/1998 |
| JP | 2000355382 | A | | 12/2000 |
| JP | 2001038256 | A | | 2/2001 |
| JP | 2001130657 | A | | 5/2001 |
| JP | 2001341767 | A | | 12/2001 |
| JP | 2001341768 | A | | 12/2001 |
| JP | 2001346878 | A | | 12/2001 |
| JP | 10108727 | A | | 4/2004 |
| WO | WO02087984 | | * | 11/2002 |
| WO | 2004080606 | A1 | | 9/2004 |

* cited by examiner

FLUID DISPENSING DEVICE WITH STOPPER

This application is filed pursuant to 35 U.S.C. §371 as a United States National Phase Application of International Patent Application Serial No. PCT/GB2004/001002 filed Mar. 11, 2004, which claims priority from Great Britain Application No. 0305583.7 filed in the United Kingdom on Mar. 11, 2003.

The present invention relates to a medicament dispenser and in particular to a fluid dispensing device for use as a nasal inhalation device for delivery of medicament.

It is well known to provide a medicament dispenser, in which fluid is dispensed via a nozzle or orifice upon the application of a force by a user to a pump dispenser. Such devices are generally arranged with a reservoir containing several doses in a fluid formulation to be dispensed by sequential metered pump actuations. An example of a pump action spray is shown and described in U.S. Pat. No. 4,946,069.

It is a problem with such prior art mechanical pumps that fluid delivered to the nozzle or orifice but not dispensed there from may under normal atmospheric pressure drain back down the interior of the nozzle and potentially into the fluid reservoir. This can lead to medicament precipitating out onto the sides of the nozzle interior and pump and also potentially to contamination of the contents of the reservoir by drained-back fluid material.

It will be appreciated that the prevention of fluid drain back is therefore desirable.

The Applicants have now found that the problem of fluid drain back may be ameliorated by the use of a stopper placed over the dispensing orifice of the nozzle. The stopper acts to prevent the normal draining back action by setting up a 'negative pressure' effect between the stoppered end and potentially draining back fluid in the nozzle tip, and thereby reduces the need to re-prime the device before the next use thereof as can be required where drain back occurs.

It is an object of the present invention to provide a fluid dispensing device, which provides reduced drain back of fluid from the nozzle.

It is a further object of the present invention to provide a fluid dispensing device, which prevents the need for priming (i.e. 're-prime') before use, as can be required for a device that permits drain back of fluid from the nozzle.

According to a first aspect of the invention there is provided a fluid dispensing device comprising a body defining a cavity and a dispensing nozzle having a dispensing orifice, a fluid discharging device housed in the cavity, the fluid discharging device having a hollow casing defining a reservoir for containing a volume of fluid and a pump having a suction inlet extending within the hollow casing, the pump having a discharge outlet extending from a first end of the hollow casing for co-operation with the dispensing nozzle to enable pumped delivery of fluid from the reservoir to the dispensing nozzle, wherein the dispensing orifice of the dispensing nozzle is provided with a reversible stopper.

The stopper acts such as to prevent drain back of delivered fluid from the dispensing nozzle (in particular, from the area at the tip of the nozzle and generally adjacent to the dispensing orifice). The stopper also acts such as to reduce fluid egress by evaporation as would tend to occur at an open (i.e. unstoppered) dispensing orifice.

The stopper is reversibly mountable to the dispensing orifice of the nozzle (e.g. at the tip). That is to say, the stopper may reversibly be arranged in both a 'storage' position, in which it locates at the dispensing orifice to prevent drain back of fluid into the nozzle and in an 'in use' position, in which it is spaced from the dispensing orifice to allow dispensing of fluid from the nozzle.

In one aspect, the nozzle tip is shaped to define an essentially flat profile. In another aspect, the nozzle aspect is shaped such as to define a well circumferential to the dispensing orifice. Where a circumferential well is so defined, the stopper herein may be arranged to extend at least partly into that well when the device is in the 'storage position'.

Suitably, the stopper is located on the exterior of the dispensing nozzle. That is to say, the stopper is not located and/or does not extend within the nozzle (i.e. not within the nozzle dispensing channel).

Suitably, the stopper is independent of the fluid discharging device, and particularly the pump and/or container thereof.

It will be appreciated that in general operation of the fluid dispensing device relative movement between the hollow casing and the pump acts such as to pump fluid from the fluid reservoir into the dispensing nozzle for dispensing therefrom.

In aspects, the pumping is metered. For example, each pumping action results in delivery of a single dose of fluid from the reservoir to the nozzle.

Suitably for metered delivery, the pump includes a plunger, which is slidable in a metering chamber located within the hollow casing, the metering chamber being sized to accommodate a single dose of fluid.

The reservoir typically contains several doses of fluid.

The stopper herein is reversibly mountable to the dispensing nozzle to enable reversible sealing of the dispensing orifice. In use, such sealing acts such as to minimise drain back of fluid from the dispensing orifice through the interior of the nozzle.

The Applicant has found that the profile of that part of the stopper that contacts the dispensing nozzle (i.e. stoppers the dispensing orifice) in the 'storage position' has a curved profile and is preferably hemispherical (e.g. dome shaped). Such hemispherical shape has been found to assist in locating the stopper at the dispensing orifice (or tip) for effective stoppering thereof.

The Applicant has also noted that if a stopper is used that has a flat (e.g. disc-shaped or squared off) contact profile there is a risk that if the stopper does not align perfectly with the dispensing nozzle orifice one part of the stopper tends to tip up and another part to tip down, thereby compromising its sealing ability. This problem does not arise in relation to the preferred hemispherical shape, which naturally tends to align the 'crest' of the hemisphere with the tip of the nozzle.

In one aspect, the hemispherical stopper is flexible enough such that in the 'storage position' a portion of the stopper extends into the dispensing orifice of the dispensing nozzle to partly fill the space therein and hence to minimise any air gap.

The stopper may have any suitable overall shape including disc shaped, wherein the disc may be flat, or in aspects have a convex or concave form.

In one preferred aspect, the stopper comprises a flat, preferably disc-shaped base and a hemispherical head element provided thereto. Overall, the stopper therefore suitably resembles a 'bowler hat' with the crest of the hat contacting the dispensing nozzle, in use to prevent drain back at the dispensing orifice. The base and head parts of the stopper may be formed separately and then brought together, or alternatively the overall 'bowler hat' shape (i.e. base and head) is moulded as a single part.

It will be appreciated that the stopper is generally shaped to optimise sealing engagement with the tip of the dispensing nozzle (i.e. that area proximal to the dispensing orifice). It also is desirable that the sealing acts such as to minimise the 'air gap' defined at the dispensing orifice when the device is in the 'storage position', preferably reducing it to close to zero. In general terms, the 'air gap' is that free volume defined in combination by the stopper, dispensing channel of the nozzle and head of fluid in the dispensing channel.

Suitably, the volume of the air gap is small enough such that any pressure drop due to an increase in this volume balances the weight of fluid below it to prevent the fluid draining back down into the pump.

Desirably, the seal provided by the stopper is fully airtight, although in practical terms where there is an initial air gap some slight seepage of air inevitably occurs over an extended time scale. The Applicant has realized that the volume of any air seepage through the seal is proportional to the difference in pressure between the air gap and ambient atmospheric pressure. Where however, the air gap has essentially zero volume (i.e. the stopper contacts the fluid in the dispensing channel such that there is no air gap) the relevant pressure difference is that between the fluid in contact with the stopper and the atmosphere and the seepage rate through the seal is drastically reduced.

The Applicant has also realized that where an air gap exists any drain back will tend to reduce the pressure in the air gap, which in turn increases the seepage past the seal having the result that the air gap increases to promote even greater drain back. Thus, drain back can promote seepage past the seal, which in turns promotes further drain back. This realization therefore provides direction to both reduce the size of the initial air gap and to ensure maximum seal integrity by the stopper since both of these factors in tandem influence subsequent drain back and seepage through the seal.

In one aspect, the shape of the stopper, particular the part that in the 'storage position' contacts the dispensing nozzle, may be arranged to inversely mirror that of the nozzle tip. In one particular aspect, at least part of the stopper has concave form and is shaped to mirror the form of a convex tip of the dispensing nozzle.

In another aspect, the tip of the dispensing nozzle is either formed from a soft, compressible material or has soft, compressible material provided thereto (e.g. as a ring of material provided around the tip) to ensure effective contact between the stopper and the tip of the dispensing nozzle for effective reduction of drain back at the dispensing orifice.

The stopper may be formed from any suitable material including those with plastic properties, particularly those with resilient properties. Stoppers made from synthetic and naturally occurring polymers including rubber are herein envisaged.

Particular stopper materials include elastomeric materials such as synthetic rubbers and Thermoplastic Elastomer (TPE) materials, including those materials sold under the trade name Santoprene by Advanced Elastomer Systems, including that material sold under the trade name Santoprene 8000 Rubber 8281-35W237.

Suitable elastomeric materials are typically employed within their elastic regime and are preferably susceptible to injection moulding techniques for forming suitable stopper shapes and particularly contact profiles (i.e. the profile of the part of the stopper that contacts the dispensing nozzle in the 'storage position').

Suitably, the stopper materials are soft enough to be reasonably compressible but hard enough to retain a shape for stoppering the dispensing orifice. The Applicant has determined that stopper materials having a hardness of from 30 to 40 Shore A, particularly from 33 to 37 Shore A, such as 35 Shore A are especially suitable.

Suitable stoppers may be formed in a variety of ways. In one aspect, a rubber disc-shaped stopper is stamped from a sheet of rubber. In another aspect, a disc-shaped stopper is moulded (e.g. by an injection moulding process).

It is envisaged that when in the 'storage position' the stopper experiences a certain compressive force such as to ensure sufficient sealing contact with the dispensing nozzle to prevent drain back at the dispensing orifice. Suitably, the amount of compressive force greater than 1.5N, typically from 2 to 6N.

The device may further comprise a protective end cap having an inner surface for engagement with the body. The end cap is moveable from a first position in which it covers the nozzle to a second position in which the nozzle is uncovered.

Suitably, the stopper locates on the end cap such that when the end cap is in the first (i.e. protective) position the stopper contacts (e.g. engages) the dispensing nozzle to seal the dispensing orifice. In the second (i.e. in-use position) the stopper is spaced from (e.g. disengaged from) the dispensing nozzle such that the dispensing orifice is no longer sealed.

The stopper may form an integral part of the end cap or alternatively, the stopper may mount to the end cap. Any suitable method of mounting is envisaged including adhesive, snap-fit and weld mounting. In general, the stopper locates in the inner part of the end cap.

In one aspect, the inner part of the end cap is provided with annular walls defining a cavity for receipt of the stopper as an insert thereto. The stopper insert may be simply be mechanically inserted within said cavity (e.g. interference fit) or it may be adhesively or otherwise fixed.

One preferred stopper insert has the 'bowler hat' form described previously, in which the stopper insert comprises a flat, preferably disc-shaped base and a hemispherical head element. The base of the stopper is inserted into the cavity defined by the annular walls such that the head faces outwards and may contact the dispensing nozzle, in use to prevent drain back at the dispensing orifice.

Suitable stopper insert forms may be formed in a variety of ways. In one aspect, a rubber disc-shaped stopper is stamped from a sheet of rubber. In another aspect, a disc-shaped stopper is moulded (e.g. by an injection moulding process). In a further aspect, the protective end cap is moulded and the stopper is then moulded within the formed end cap (i.e. a 'two shot' moulding process).

In one particular aspect, the inner part of the end cap is provided with an annular wall or walls defining a cavity for receipt of the stopper as an insert thereto and that end cap is formed as a moulding and the stopper insert is provided as a second moulding thereto (i.e. by way of a second moulding operation in an overall 'two shot' moulding process). In a variation of this aspect, the material provided as in the second moulding operation may extend beyond the stopper to form other parts of the end cap (e.g. in one aspect to form a mounting for mounting the end cap to a body of the dispensing device).

In another particular aspect, the inner part of the end cap is provided with an annular wall or walls defining a cavity for receipt of the stopper as an insert thereto and the stopper insert has a concertina form such that it may readily compress to accommodate the form of the dispensing nozzle for effective sealing of the dispensing orifice.

In a further particular aspect, the inner part of the end cap is provided with an annular wall or walls defining a cavity for receipt of the stopper as an insert thereto and the stopper insert has a roller ball form. The annular walls are thus shaped with mounting elements (e.g. arms or pins) for mounting the roller ball within the cavity. In use, the roller ball contacts the dispensing nozzle for effective sealing of the dispensing orifice.

In another aspect, the inner part of the end cap is provided with an annular wall or walls protruding into the cap interior and a thin end wall provided thereto. In use, the thin end wall contacts the dispensing nozzle tip and thereby acts as a stopper to prevent drain back at the dispensing orifice. The annular wall or walls may either be rigid or flexible (e.g. susceptible to flexing in concertina-fashion). The thin wall is typically flexible such that it may accommodate the form of the dispensing nozzle tip for effective sealing of the dispensing orifice. In embodiments, a plug is provided to fit in the cavity defined by the annular walls and end wall to prevent damage thereto.

The end cap is suitably arranged for guided receipt by the body, in particular to ensure best alignment of the stopper and dispensing orifice of the nozzle in the 'storage position'. The end cap may in particular, be provided with guide projections (e.g. legs) arranged for receipt by apertures and/or channels defined within the body and arranged for correct alignment of end cap with body. In aspects, the projections include lugs or other retaining means for reversibly retaining the end cap to the body.

The Applicant has however, noted that screw engagement of the end cap with body can be problematic in that the screw action may result in frictional contact between the stopper insert of the end cap and the dispensing nozzle that may cause the stopper insert to become detached from the end cap.

The end cap is suitably formed from a rigid material and one that does not tend to creep during its lifetime. A suitable end cap material is that sold under the trade name Terluran GP-22 Natural by BASF Plastics.

The hollow casing may take any suitable form. Suitably, several lugs are formed on the hollow casing for engagement with complementary projections formed on the inner surface of the end cap, each of the lugs being arranged to extend through a longitudinally extending slot formed in the side wall of the body.

The hollow casing may have at least one outwardly extending detent for engagement with a complementary recess formed in the inner surface of the end cap so as to releasable hold the end cap in position on the body.

Each detent may extend through a respective longitudinally extending slot in the body for engagement with the respective recess formed in the end cap.

In one aspect, the fluid discharging device is moveably housed within the housing, the fluid discharging device having a longitudinal axis and the fluid dispensing device is provided with finger operable means moveable with respect to the longitudinal axis of the fluid discharging device to apply a force to the container to move the container along the longitudinal axis towards the nozzle so as to actuate the compression pump.

The term finger operable means is meant to encompass such means operable by action of the finger or thumb, or combinations thereof of a typical user (e.g. an adult or child patient).

In one aspect, the finger operable means is moveable transversely with respect to the longitudinal axis of the fluid discharge device to apply a force directly or indirectly to the container. In another aspect, the finger operable means is moveable generally parallel to the longitudinal axis of the fluid discharge device to apply a force directly or indirectly to the container. Other movements intermediate between 'transverse' and 'parallel' are envisaged. In variations, the finger operable means may contact the container or be coupled thereto to enable the necessary transfer of force.

Suitably, the finger operable means is arranged to apply mechanical advantage. That is to say, the finger operable means applies mechanical advantage to the user force to adjust (generally, to enhance or smooth) the force experienced by the container. The mechanical advantage may in one aspect, be provided in either a uniform manner such as by a constant mechanical advantage enhancement, for example by a ratio of from 1.5:1 to 10:1 (enhanced force: initial force), more typically from 2:1 to 5:1. In another aspect, the mechanical advantage is applied in a non-constant manner such as progressive increase or progressive decrease of mechanical advantage over the applied force cycle. The exact profile of mechanical advantage variation may be readily determined by reference to the desired spray profile and all relevant characteristics of the device and formulation to be sprayed (e.g. viscosity and density).

Suitably, the finger operable means has a form, which naturally gives rise to mechanical advantage such as a lever, cam or screw form.

The finger operable means may comprise of at least one lever pivotally connected to part of the housing and arranged to transfer force to the container (e.g. acting directly thereupon) so as to urge the container towards the nozzle when the or each lever is moved by a user.

In one aspect, there are two opposing levers, each of which pivotally connect to part of the housing and may be arranged to act upon the container so as to urge the container towards the nozzle when the two levers are squeezed together by a user.

Alternatively, the finger operable means may comprise of at least one lever to apply a force to an actuating means used to move the container towards the nozzle so as to actuate the pump.

In which case the or each lever may be pivotally supported at a lower end within the housing and the actuating means may in aspects be connected to a neck of the container (e.g. formed as a collar thereto).

Suitably, there may be two opposing levers, each of which is pivotally supported near a lower end of the housing and may be arranged to act upon the actuating means so as to urge the container towards the nozzle when the two levers are squeezed together by a user.

Alternatively, the finger operable means may comprise of at least one lever slidably supported within the housing to apply a force to the container so as to move the container towards the nozzle and actuate the compression pump.

Suitably, the fluid dispensing device further comprises a lock for reversibly locking the finger operable means to prevent unintended movement thereof.

The lock may comprise any suitable locking means, but is preferably of relatively simple form. Suitably, the lock comprises a mechanical locking element such as a tab, clip, lug or peg.

In one aspect, the locking element is engageable with both the housing and the finger operable means to prevent relative movement there between. Suitably, the locking element engages with a locking portion of the housing and finger operable means such as a recess or aperture provided thereto.

In one particular aspect, the locking element is provided to a protective end cap reversibly receivable by the housing to reversibly cover the nozzle. Suitably, the locking element protrudes from the cap (e.g. taking the form of a tab, clip, lug or peg provided thereto) such that when the cap is received by the housing the locking element engages with the housing and finger operable means to prevent relative movement there between, but when the cap is removed from the housing (i.e. nozzle uncovered position) the locking element is also removed from engagement with at least one of, preferably both of, the housing and finger operable means.

In another aspect, the locking element is provided to the housing and is engageable with the finger operable means to prevent relative movement there between. Suitably, the locking element engages with a locking portion of the finger operable means such as a recess or aperture provided thereto.

In another aspect, the locking element is provided to the finger operable means and is engageable with the housing to prevent relative movement there between. Suitably, the locking element engages with a locking portion of the housing such as a recess or aperture provided thereto.

Suitably, a pre-load means is provided to prevent actuation of the compression pump until a pre-determined force is applied to the finger operable means. The pre-load means acts such as to prevent actuation of the compression pump until a pre-determined force is applied to the finger operable means. The pre-determined force may thus, be thought of as a 'threshold' or 'barrier' force which must first be overcome before actuation of the compression pump can occur.

The quantum of pre-determined force that is to be overcome before actuation of the compression pump is enabled is selected according to various factors including characteristics of the pump, typical user profile, nature of the fluid and the desired spray characteristics.

Typically, the pre-determined force is in the range from 5 to 30N, more typically from 10 to 25N. That is to say, typically from 5 to 30N, more typically from 10 to 25N of force must be applied to the finger operable means before actuation of the compression pump is enabled. Such values tend to correspond to a force which prevents a suitable 'barrier force' to a weak, nondescript or unintended finger movement whilst readily being overcome by the determined finger (or thumb) action of a user. It will be appreciated that if the device is designed for use by a child or elderly patient it may have a lower pre-determined force than that designed for adult usage.

In one aspect, the pre-load means is physically interposed between the or each finger operable means (e.g. lever) and the container.

In which case, the pre-load means may comprise of a step formed on the container which must be ridden over by the or each lever before the compression pump can be actuated wherein the step is over-ridden when the pre-determined force is applied to the or each lever.

Alternatively, the pre-load means may comprise of a step formed on the or each finger operable means (e.g. lever) which must be ridden over by the container before the compression pump can be actuated wherein the step is over-ridden when the pre-determined force is applied to the or each lever.

In yet a further alternative, the pre-load means may comprise of at least one detent formed on one of the container or the or each finger operable means (e.g. a lever) and a recess formed on the other of the container or the or each lever wherein the or each detent is able to ride out of the recess with which it is engaged when the pre-determined force is applied to the or each lever.

In another aspect, the pre-load means is interposed between the housing and the container.

In which case, the pre-load means may comprise of one or more detents formed on the container for engagement with part of the housing, the or all of the detents being disengageable from the housing when the pre-determined force is applied to the finger operable means so as to allow the compression pump to be actuated.

Alternatively, the pre-load means may comprise of one or more detents formed on the housing for engagement with part of the container, the or all of the detents being disengageable from the container when the pre-determined force is applied to the finger operable means so as to allow the compression pump to be actuated.

In another aspect, the pre-load means is interposed between the container and the discharge tube.

In which case, the pre-load means may comprises of a step formed on the discharge tube and at least one latching member attached to the container, the arrangement being such that, when the pre-determined force is applied to the finger operable means, the or each latching member is able to ride over the step so as to allow the compression pump to be actuated.

Alternatively, the pre-load means may comprise of a recess formed on the discharge tube and at least one latching member attached to the container, the arrangement being such that, when the pre-determined force is applied to the finger operable means, the or each latching member is able to ride out of the recess so as to allow the compression pump to be actuated.

In another aspect, the pre-load means is interposed between the housing and the or each finger operable means (e.g. lever).

In which case, the pre-load means may comprise of at least one detent formed on the housing for engagement with each lever, the or all of the detents being disengageable from the respective lever when the pre-determined force is applied to the or each lever so as to allow the compression pump to be actuated.

Alternatively, the pre-load means may comprise of at least one detent formed on each lever for engagement with part of the housing, the or all of the detents being disengageable from the housing when the pre-determined force is applied to the or each lever so as to allow the compression pump to be actuated.

In another aspect, the pre-load means is interposed between the actuating means and the housing.

In which case, the pre-load means may comprise of at least one detent formed on part of the actuating means for engagement with part of the housing, the or all of the detents being disengageable from the housing when the pre-determined force is applied to the or each finger operable means (e.g. lever) so as to allow the compression pump to be actuated.

Alternatively, the pre-load means may comprise of at least one detent formed on part of the housing each detent being arranged for engagement with a complementary recess formed on part of the actuating means, each detent being disengageable from its respective recess when the pre-determined force is applied to the or each finger operable means (e.g. lever) so as to allow the compression pump to be actuated.

In another aspect, the pre-load means is interposed between the or each finger operable means (e.g. lever) and the respective actuating means.

In which case, the pre-load means may comprise of at least one detent formed on the or each lever for engagement with a respective recess formed on part of the actuating means, each detent being disengageable from its respective complementary recess when the pre-determined force is applied to the lever so as to allow the compression pump to be actuated.

Alternatively, the pre-load means comprises of at least one detent formed on each actuating means for engagement with a recess formed on a respective lever, each detent being disengageable from its respective complementary recess when the pre-determined force is applied to the lever so as to allow the compression pump to be actuated.

As yet a further alternative, the pre-load means may comprise of an actuating device having a variable mechanical ratio such that until the pre-determined force is applied to the or each finger operable means (e.g. a lever) no significant force is transferred to the container along the longitudinal axis.

The fluid dispensing device may alternatively comprise of a finger operable means in the form of a single lever and the pre-load means may further comprise of a spring interposed between the lever and the container, the spring being used to urge the is container towards the nozzle so as to actuate the compression pump.

In which case the spring may be compressed by movement of the lever until the pre-determined force is applied (i.e. by a combination of user-applied force and stored spring force), at which point the threshold of the pre-load means used to prevent actuation of the compression pump is overcome by the force being applied to the container such that the container moves rapidly towards the nozzle so as to actuate the compression pump.

Suitably, the fluid dispensing device is additionally provided with force modifying means for modifying the force applied to the container. That is to say, means for modifying the force applied to (and therefore, ultimately acting on) the container compared to that force directly applied to the finger operable means by the user.

Suitably, the force modifying means acts such as to amplify the force applied (i.e. it comprises force amplifying means). The amplification may be provided in either a uniform manner such as by a constant amplification, for example by a ratio of from 1.5:1 to 10:1 (amplified force: initial force; i.e. degree of amplification of from 1.5 to 10), more typically from 2:1 to 5:1. In another aspect, the amplification is applied in a non-constant manner such as progressive increase or progressive decrease of mechanical advantage over the applied force cycle.

The exact profile of force modification may be readily determined by reference to the desired spray profile and all relevant characteristics of the device and formulation to be sprayed (e.g. viscosity and density).

The force modifying means may in one aspect, be integral with the finger operable means. In this aspect, the force modifying means may comprise an aspect of the finger operable means shaped to give rise to a mechanical advantage (e.g. a lever, cam or screw feature).

In another aspect, the force modifying means is located non-integral with the finger operable means, and typically between the finger operable means and the container. Again this aspect, the force modifying means may comprise an aspect of the finger operable means shaped to give rise to a mechanical advantage (e.g. a lever, cam or screw feature).

In one aspect, the force modifying means only acts (i.e. only acts to modify the user applied force) once the pre-determined force has been overcome. In preferred aspects, the modifying force acts such that once the pre-determined force has been overcome the force applied to the container is either relatively constant or increases on a relatively constant basis.

In one particular aspect, the force modifying means additionally comprises a stop feature, which acts to stop force being applied to the container once either a particular maximum force is reached or more typically, once the container has been moved a particular distance. In one aspect, the stop functions to prevent excess force being applied to the compression pump.

Suitably, the pump comprises a pre-compression pump, such as a VP3, VP7 or modifications, model manufactured by Valois SA. Typically, such pre-compression pumps are typically used with a bottle (glass or plastic) container capable of holding 8-50 ml of a formulation. Each spray will typically deliver 25-150 μl, particularly 50-100 μl of such a formulation and the device is therefore typically capable of providing at least 50 (e.g. 60 or 100) metered doses.

Other suitable fluid discharge devices include those sold by Erich Pfeiffer GmbH, Rexam-Sofab and Saint-Cobain Calmar GmbH.

According to another aspect of the invention there is provided a fluid dispensing apparatus for housing a fluid discharging device, the fluid dispensing apparatus comprising a body defining a cavity; and a dispensing nozzle having a dispensing orifice, wherein the dispensing orifice of the dispensing nozzle is provided with a reversible stopper.

The fluid dispensing apparatus may further comprise an end cap for engagement with the body wherein the end cap includes a stopper. The end cap may take any of the forms previously described.

In one aspect, the fluid dispensing apparatus may be provided separately from the fluid discharging device. In another aspect, the fluid dispensing apparatus and fluid discharging device are provided as a kit of parts.

According to a further aspect of the present invention there is also provided an end cap suitable for use with a dispensing device or apparatus herein, wherein the end cap includes a stopper for reversible stoppering of a dispensing orifice of a dispensing nozzle of the device or apparatus. The end cap may take any of the forms previously described.

According to a further aspect of the present invention there is provided the use of a stopper to reversibly stop up (e.g. plug or seal) the dispensing orifice of a dispensing nozzle of a dispensing device herein to prevent drain back of delivered fluid from the dispensing nozzle (in particular, from the area at the tip of the nozzle and generally adjacent to the dispensing orifice).

The device and method herein are in particular, designed to prevent drain back at the dispensing orifice of the nozzle to the pump. Based upon a shot volume (i.e. volume of fluid delivered in one actuation) of 50 μl from a typical nasal medicament dispenser device, the device and method herein suitably reduce drain back such that any reduction in shot volume related thereto is less than 3 μl, preferably less than 2 μl over a period of 14 days when stored at 25° C. and ambient pressure.

The invention will now be described further with reference to the accompanying drawing in which:—

Figure 7:
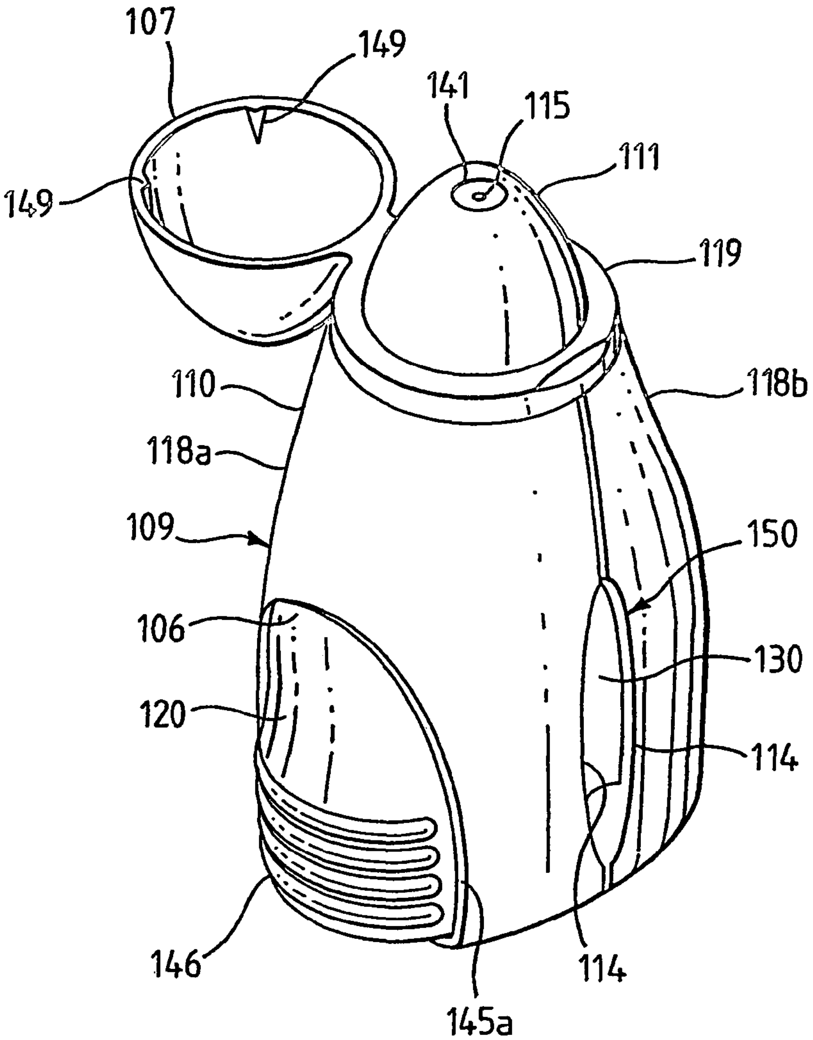
FIG. 7 is a view similar to that of FIG. 6 but viewed from a front left hand corner showing the fluid dispensing device in a ready for use state with the protective end cap removed.
Figure 7A:
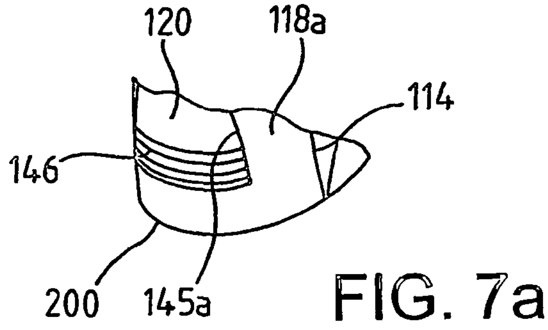
Figure 8:
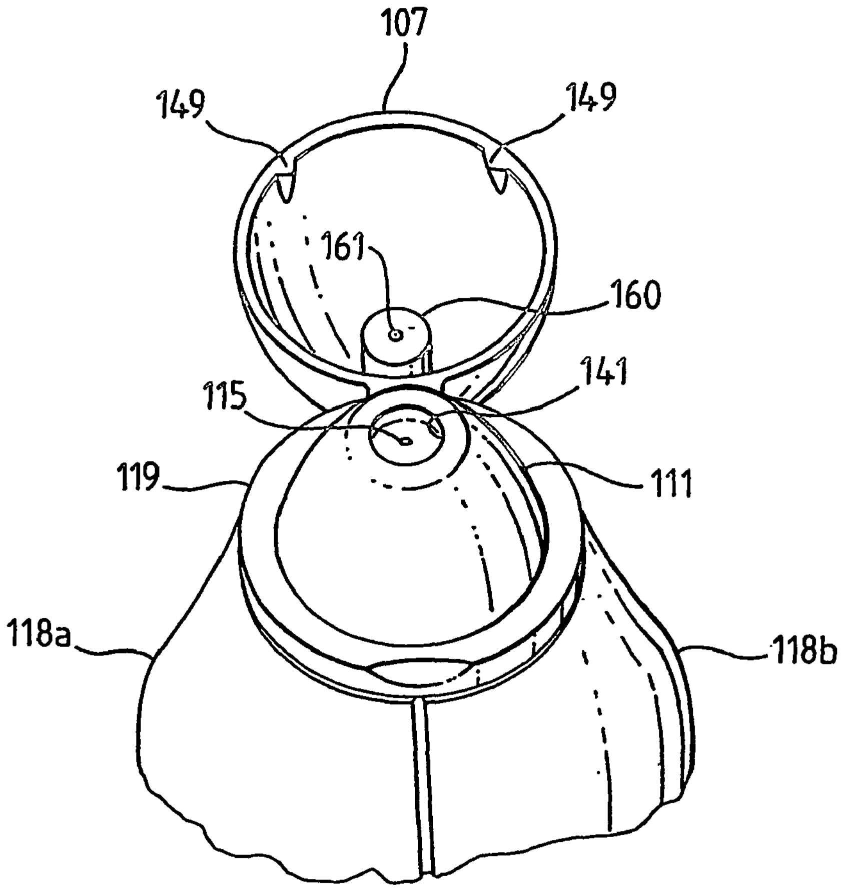
Figure 8A:
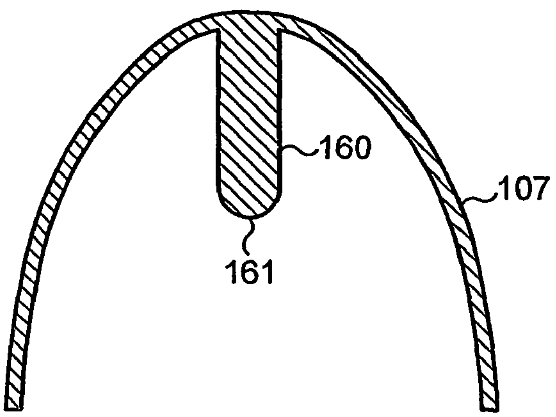
Figure 9:
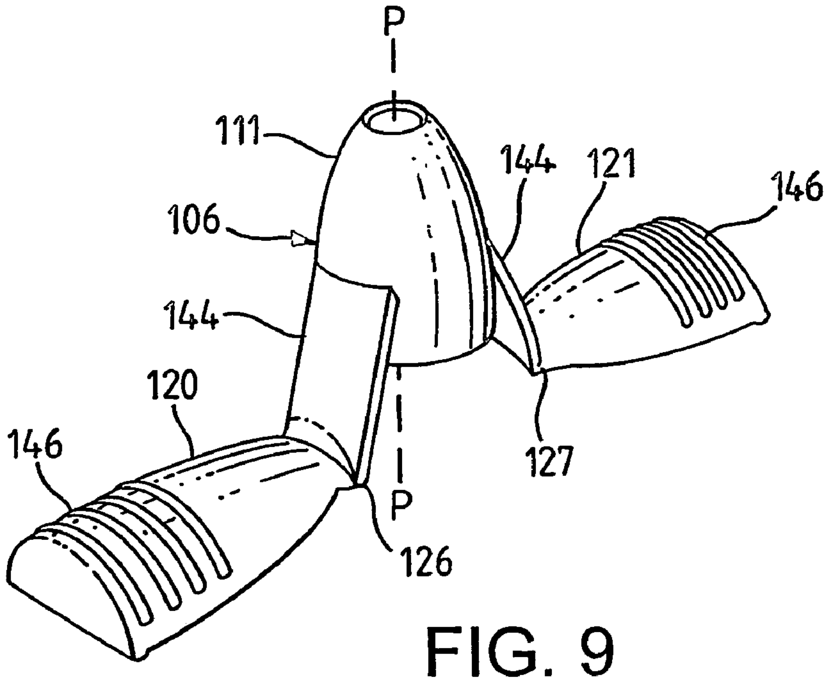
Figure 10:
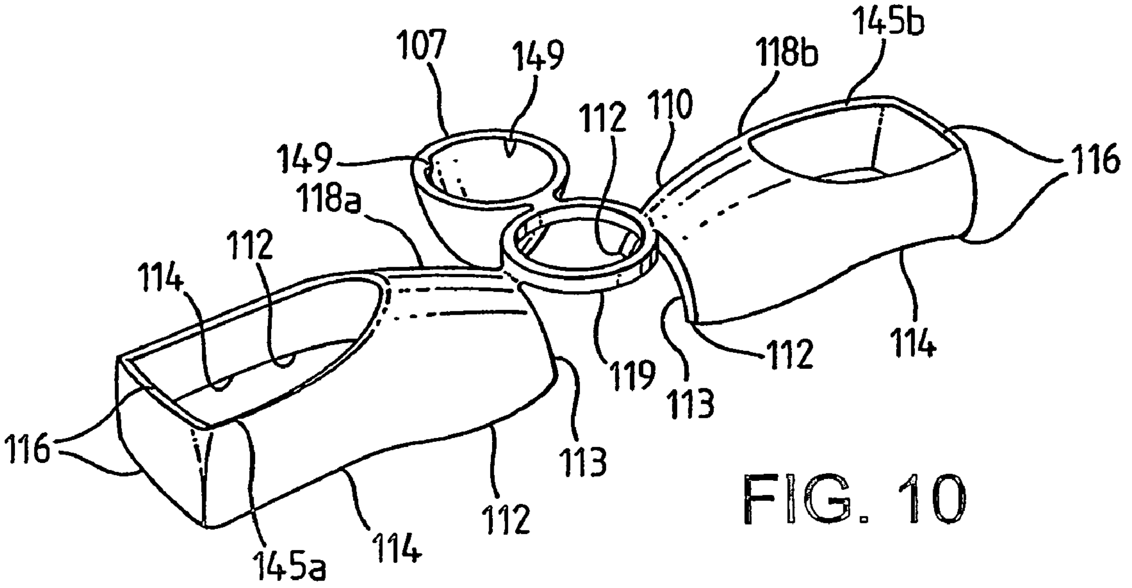
Figure 12:
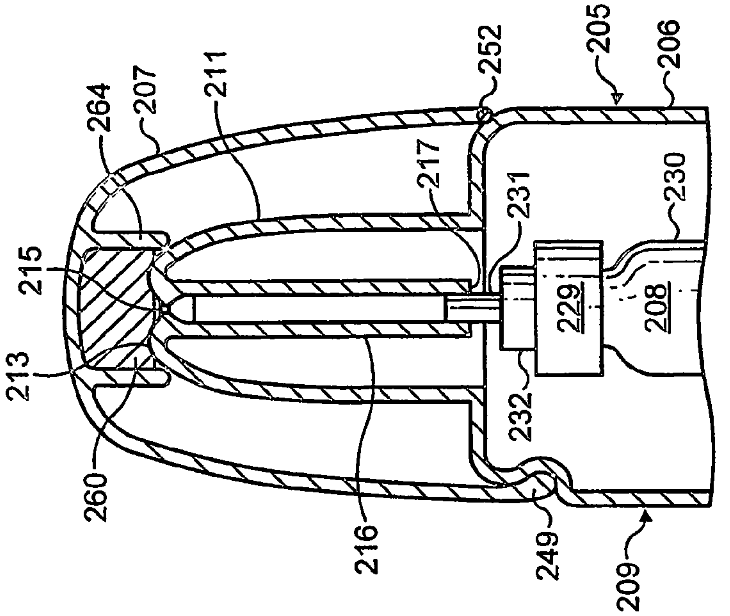
Figure 11:
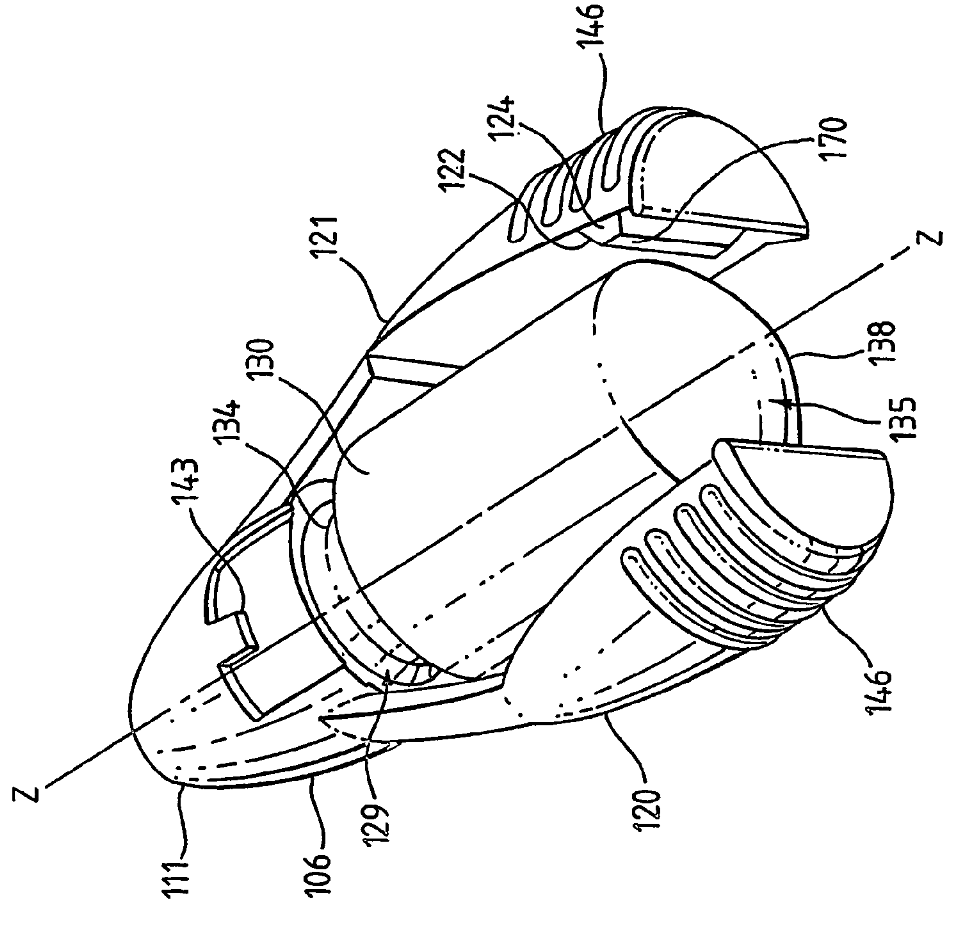
Figure 13A:
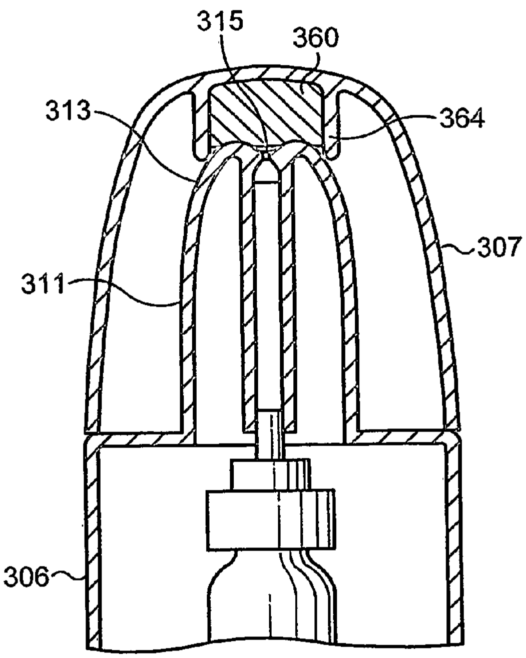
Figure 13B:
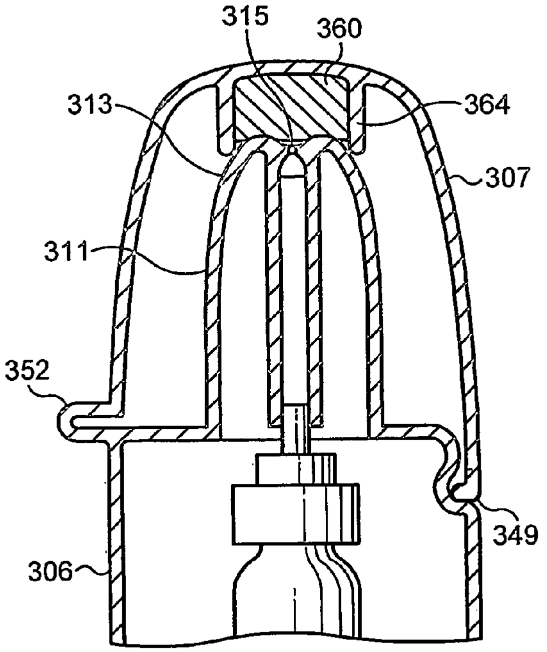
Figure 13C:
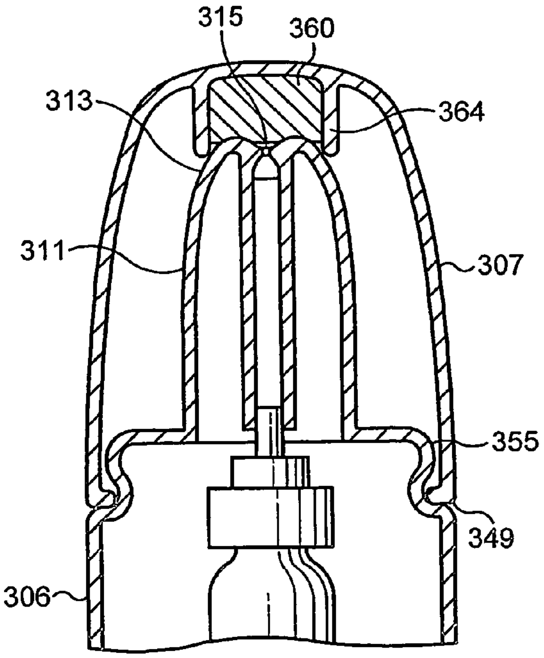
Figure 14A:
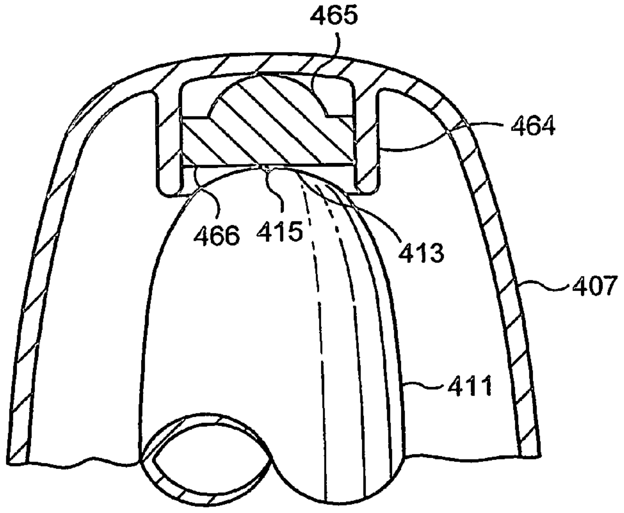
Figure 14B:
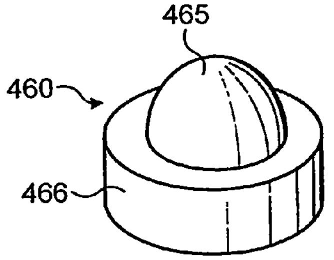

FIG. 7*a* is a scrap view of part of the fluid dispensing device shown in FIG. 7 showing a modification to the device;

FIG. 8 is an enlarged pictorial view from the front and above of a top portion of the fluid dispensing device shown in FIG. 7;

FIG. 8*a* shows a cross-sectional view of the end cap of the fluid dispensing device of FIG. 8;

FIG. 9 is a pictorial view of a body member forming part of the fluid dispensing device shown in FIG. 7 in a pre-assembled condition;

FIG. 10 is a pictorial view of a cover member forming part of the fluid dispensing device shown in FIG. 7 in a pre-assembled condition;

FIG. 11 is a pictorial view of the body member shown in FIG. 9 in a partly assembled condition in which a fluid discharge device according to the second aspect of the invention has been inserted;

FIG. 12 is a cut-away sectional view of part of a third fluid dispensing device herein;

FIGS. 13*a* to 13*c* are sectional views of the detail of stoppered end caps in variations of fluid dispensing devices herein;

FIG. 14*a* is a cross-sectional detail view of the relation of an end cap and stopper to a dispensing nozzle herein; FIG. 14*b* is a perspective view of the stopper part of FIG. 14*b;*

Figure 15:
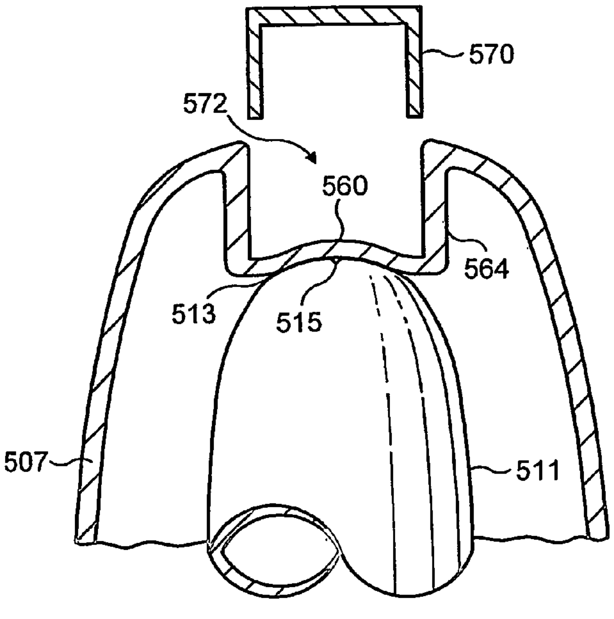
Figure 16:
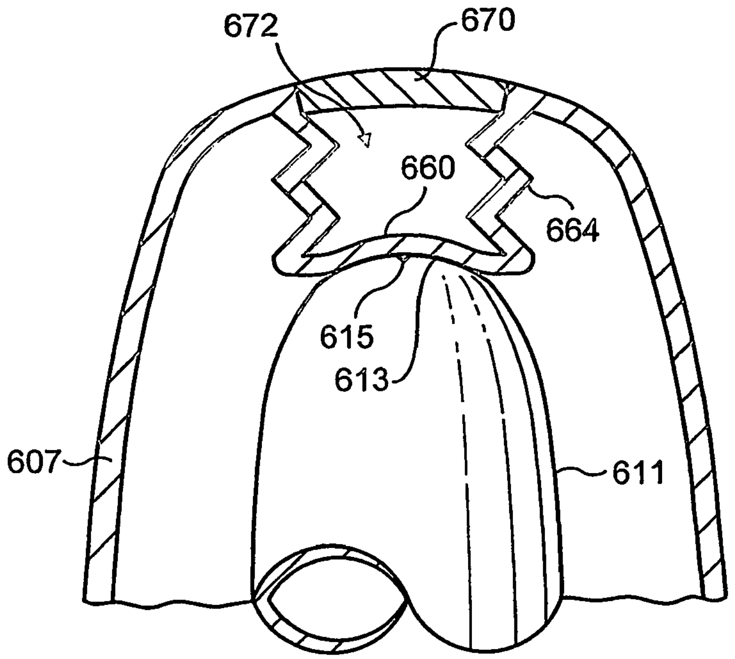
Figure 17:
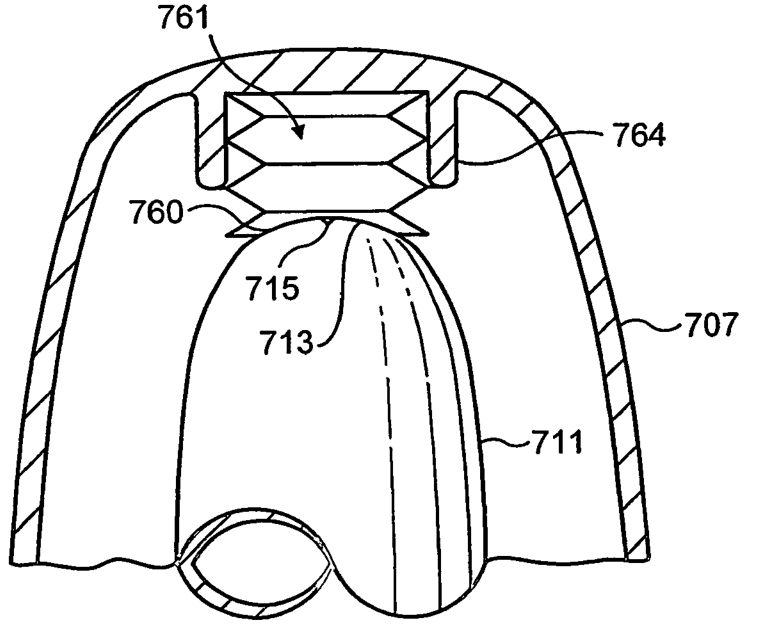
Figure 18:
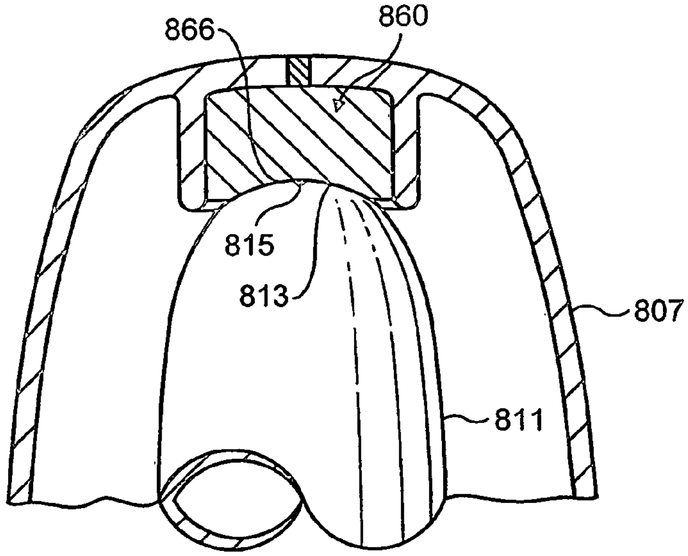
Figure 19:
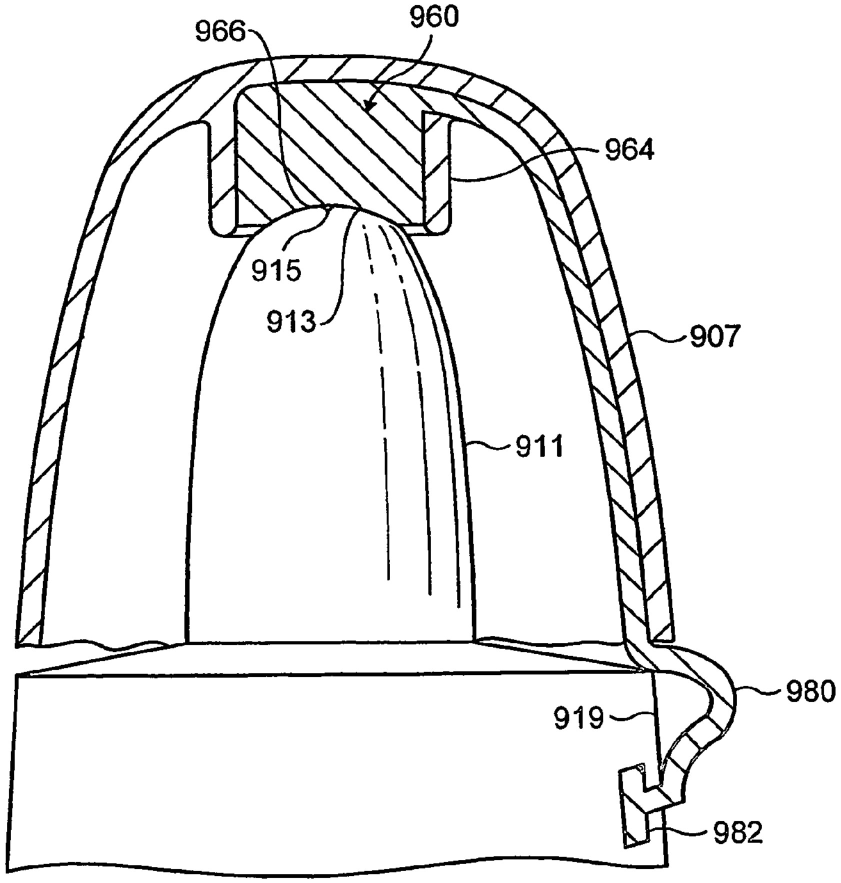
Figure 20:
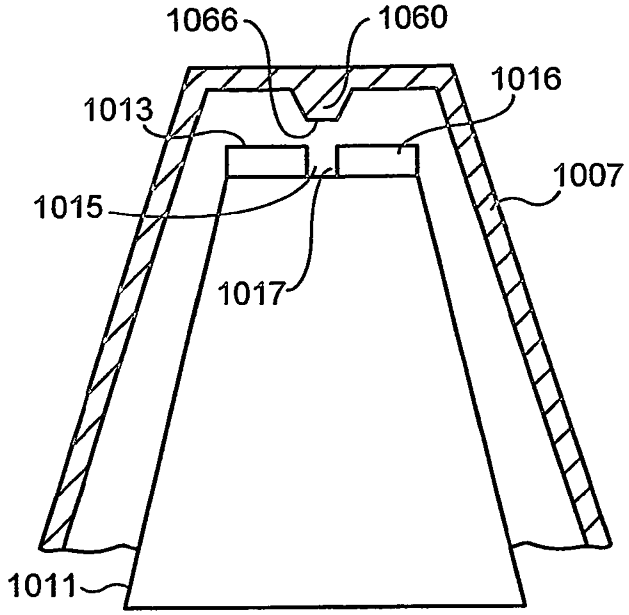
Figure 21:
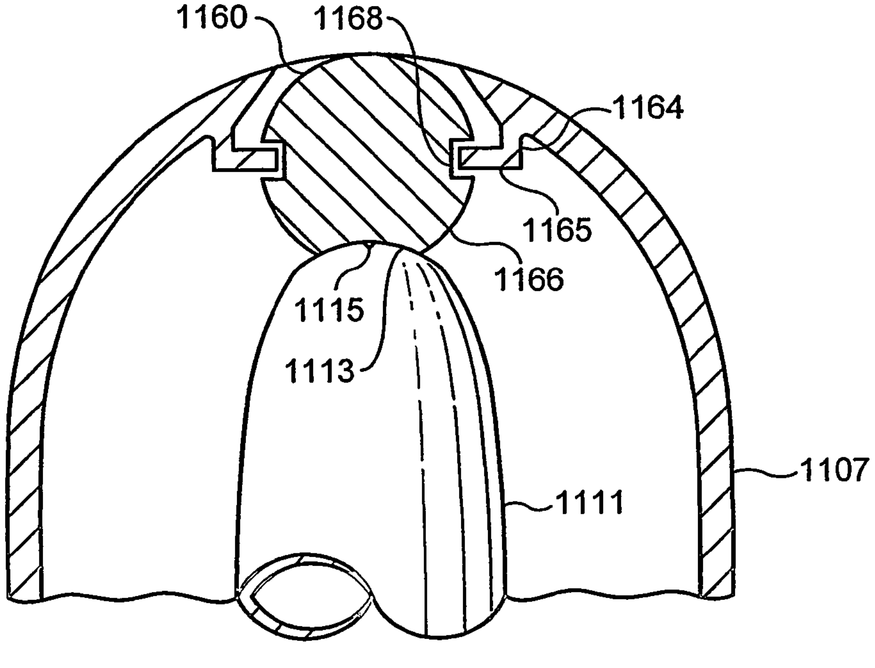
Figure 22:
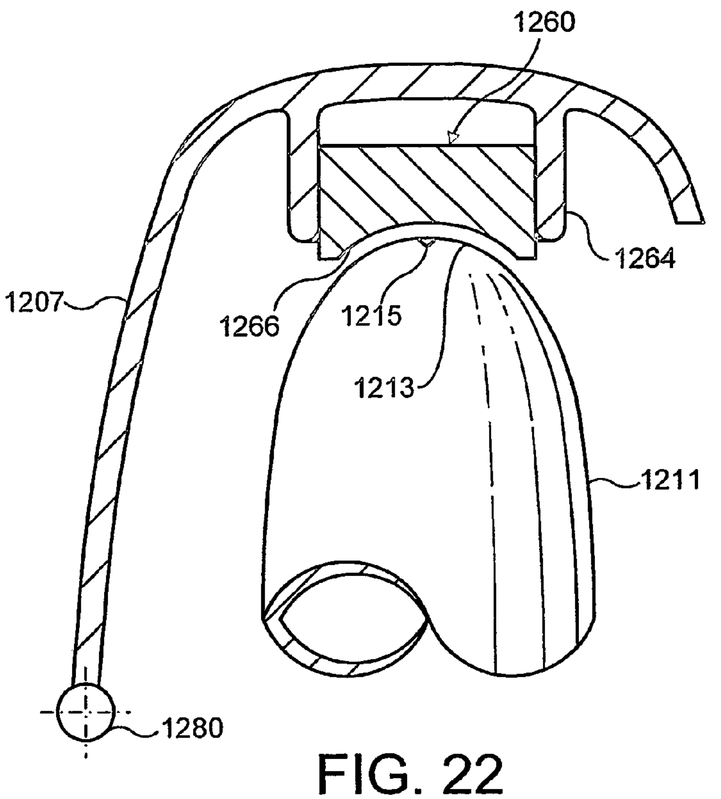
Figure 23:
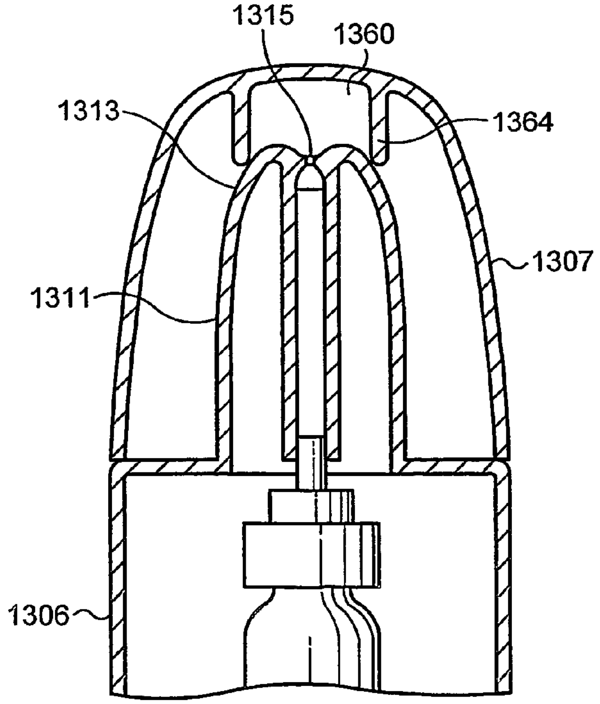
Figure 24B:
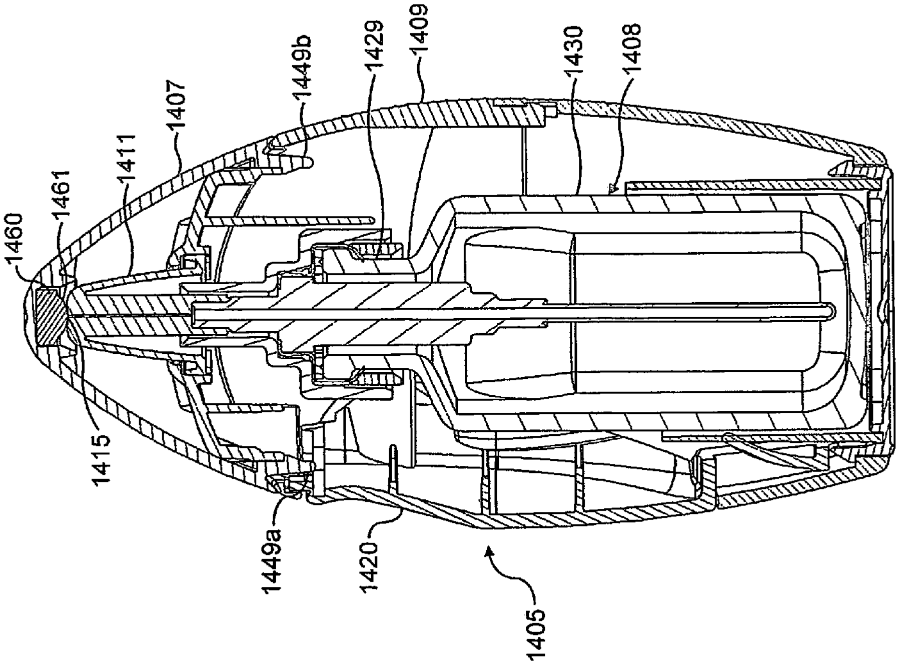
Figure 24A:
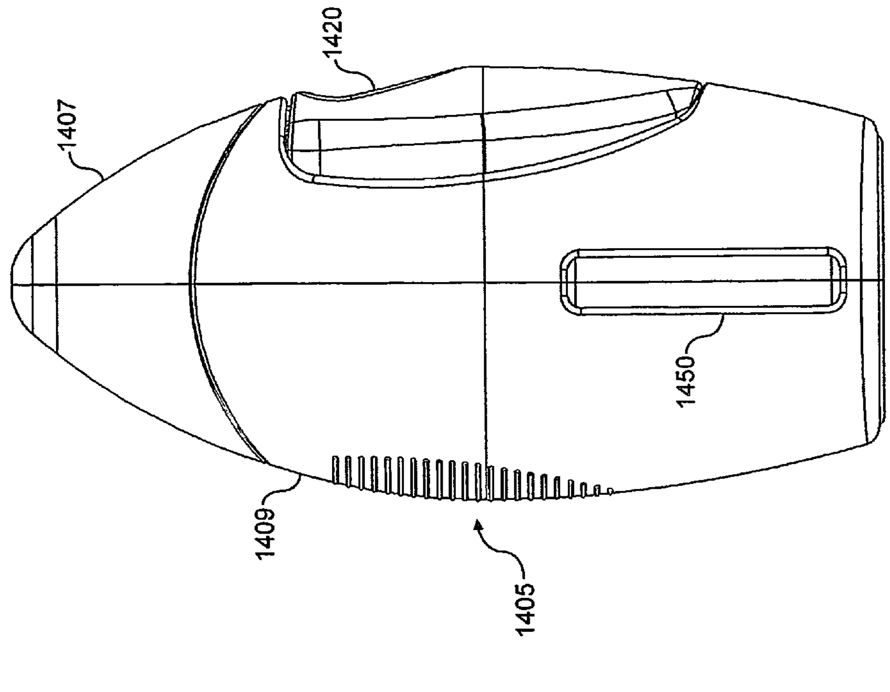
Figure 24C:
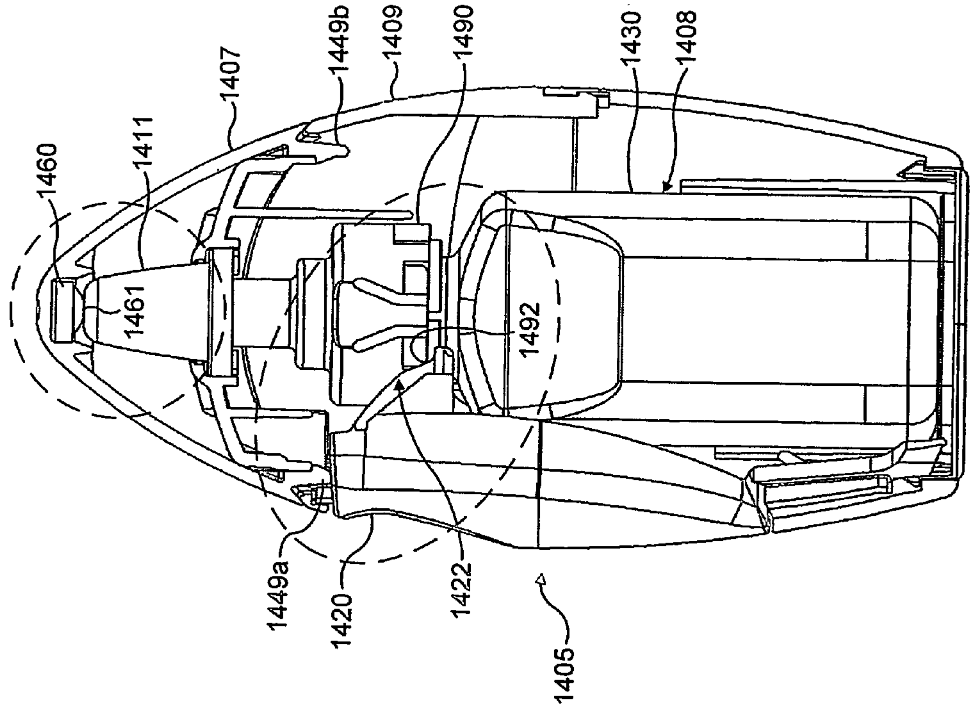
Figure 24D:
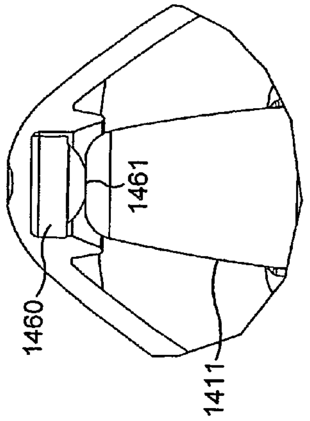
Figure 24E:
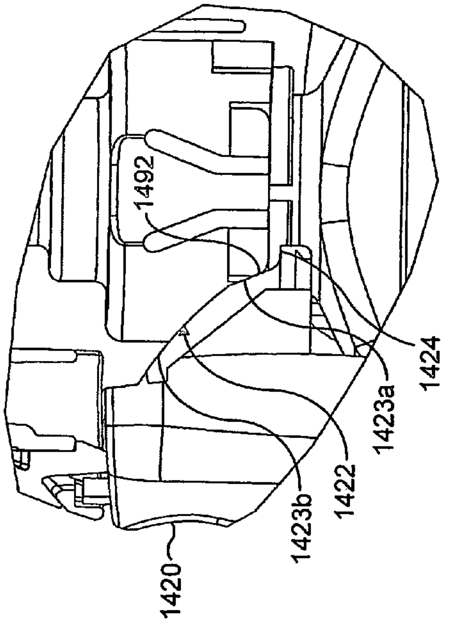

FIG. 15 is a cross-sectional, part-exploded detail view of the relation of an end cap, end cap top insert and stopper to a dispensing nozzle herein;

FIG. 16 is a cross-sectional detail view of the relation of another end cap, end cap top insert and stopper to a dispensing nozzle herein;

FIG. 17 is a cross-sectional detail view of the relation of another end cap and stopper to a dispensing nozzle herein;

FIG. 18 is a cross-sectional detail view of the relation of yet another end cap and stopper to a dispensing nozzle herein;

FIG. 19 is a cross-sectional detail view of the relation of yet another end cap and stopper to a dispensing nozzle herein;

FIG. 20 is a cross-sectional detail view of the relation of yet another end cap and stopper to a dispensing nozzle herein;

FIG. 21 is a cross-sectional detail view of the relation of yet another end cap and stopper to a dispensing nozzle herein;

FIG. 22 is a cross-sectional detail view of the relation of yet another end cap and stopper to a dispensing nozzle herein;

FIG. 23 is a sectional view of the detail of an interference fit end cap in a variation of the fluid dispensing device herein; and FIG. 24*a* to 24*c* respectively show side, sectional and part sectional views of a further dispensing device herein, and FIGS. 24*d* and 24*e* show sectional enlarged views of parts thereof.

With reference to FIGS. 1 to 5 there is shown a first embodiment of a fluid dispensing device 5 for spraying a fluid into a body cavity comprising a housing 9, a nozzle 11 for insertion into a body cavity, a fluid discharge device 8 moveably housed within the housing 9, the fluid discharge device 9 comprising a container 30 for storing the fluid to be dispensed and a compression pump 29 having a suction inlet 32 located within the container 30 and a discharge outlet 31 for transferring fluid from the pump 29 to the nozzle 11 and finger operable means 20, 21 to apply a force to the container 30 to move the container 30 towards the nozzle 11 so as to actuate the pump 29. The finger operable means being in the form of two opposing levers 20, 21 each of which is pivotally connected to part of the housing 9 and is arranged to act upon a base portion 35 of the container 30 so as to urge the container 30 towards the nozzle 11 when the two levers 20, 21 are squeezed together by a user.

In more detail the fluid dispensing device 5 comprises of a plastic moulded body 6 and the fluid discharge device 8 and further comprises of a protective end cap 7 having an inner surface for engagement with the body 6 to protect the dispensing nozzle 11.

The body 6 is made from a plastic material such as polypropylene and defines a housing 9 and a dispensing nozzle 11 so that the housing 9 and the nozzle 11 are made as a single plastic component.

The housing 9 defines a cavity 10 formed by a front wall 12, a rear wall 13 and first and second end walls 14*a*, 14*b*. The dispensing nozzle 11 is connected to one end of the housing 9, extends away from the housing 9 and has an external tapering form. It will be appreciated that the shape of the housing need not be oval it could be cylindrical or any other convenient shape.

At least one of the front wall 12 and the rear wall 13 has an aperture 28 therein to view the level of the fluid in the container 30 and in the embodiment shown there are apertures 28 in the front and rear walls 12, and 13 to view the level of the fluid in the container 30.

The discharge outlet from the pump 29 is in the form of a tubular delivery tube 31 and a tubular guide in the form of an outlet tube 16 is formed within the nozzle 11 to align and locate the delivery tube 31 correctly with respect to the nozzle 11.

An annular abutment 17 is formed at the end of the outlet tube 16. The annular abutment 17 defines the entry to a nozzle orifice 15 through which fluid can be dispensed in use and is arranged for abutment with an end of the delivery tube 31.

Figure 1:
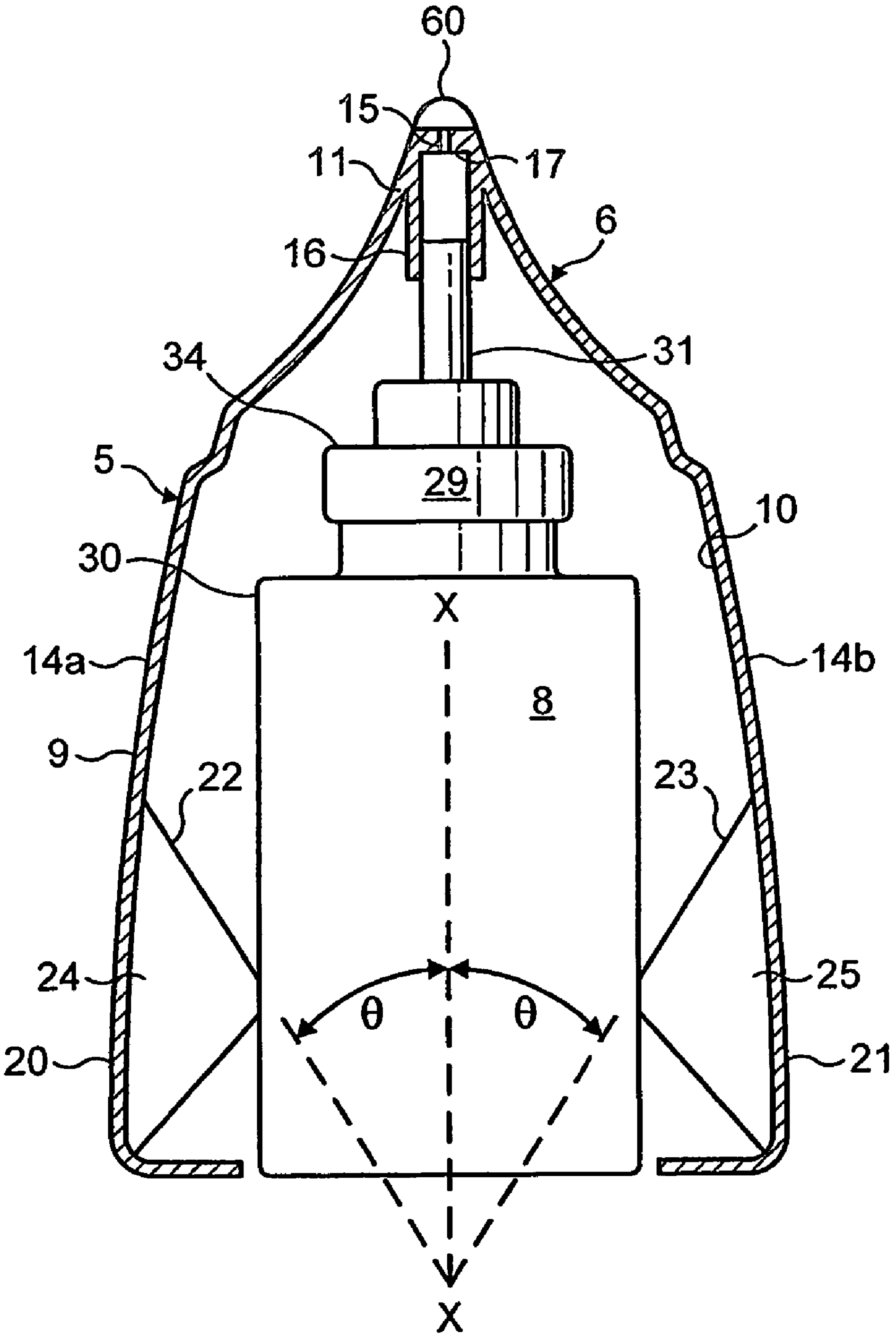
FIG. 1 is a cross-section through a first embodiment of a fluid dispensing device according to the invention in a stoppered state.
Figure 2:
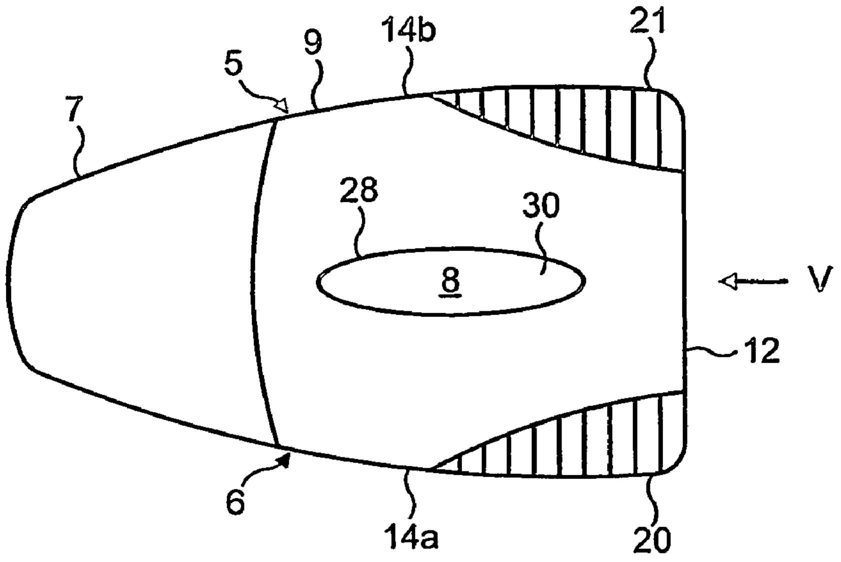
FIG. 2 is a front view of the fluid dispensing device shown in FIG. 1 in a closed or stored condition with the fluid dispensing device laid on one side.
Figure 3:
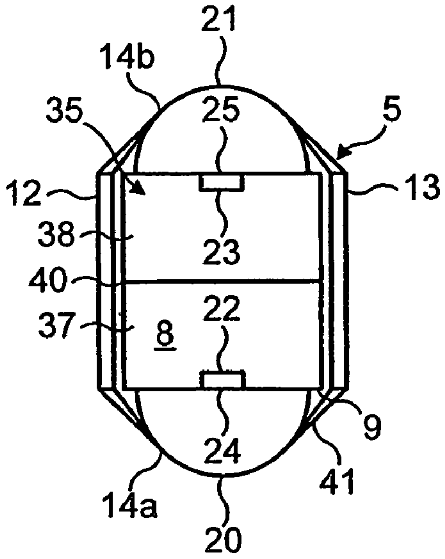
FIG. 3 is an end view of the fluid dispensing device shown in FIG. 2 in the direction of arrow 'V' on FIG. 2.

In the stoppered (storage) state of FIG. 1, rubber hemispherical nozzle stopper end 60 is reversibly mounted on annular abutment 17 to seal the nozzle orifice 15.

The fluid discharge device 8 has a longitudinal axis X-X and each of the levers 20, 21 has an abutment surface 22, 23 arranged at an angle θ to the longitudinal axis X-X of the fluid discharge device 8 for abutment against a base portion 35 of the container so as to convert a force applied to the levers 20, 21 substantially transversely to the longitudinal axis X-X of the fluid discharge device 8 into a force along the longitudinal axis X-X of the fluid discharge device 8.

This arrangement allows a standard fluid discharge device to be used without modification.

The nozzle 11 has a longitudinal axis Y-Y and the longitudinal axis X-X of the fluid discharge device 8 is aligned with the longitudinal axis Y-Y of the nozzle 11. This has the advantage that when the pump 29 is actuated the force applied to the tubular delivery tube 31 is along the axis of the tubular delivery tube and no bending or deflection of the delivery tube 31 will occur due to the applied force.

At least part of the surface of the base portion 35 of the container 30 is inclined at an angle ϕ with respect to the longitudinal axis X-X of the fluid discharge device 8 so as to form an inclined surface, the or each inclined surface being arranged to be acted upon by the levers 20, 21 so as to convert a force applied to the levers 20, 21 substantially transversely to the longitudinal axis X-X of the fluid discharge device 8 into a force along the longitudinal axis X-X of the fluid discharge device 8.

Although in the disclosed embodiment both the levers and the container have surfaces inclined to the longitudinal axis of the fluid discharge device and that in the disclosed embodiment the angle θ is approximately equal to the angle ϕ this need not be the case. Only the container or the levers need have an inclined surface or some other arrangement to apply the force from the levers to the container could be used.

The base portion 35 of the container 30 has two inclined surfaces 37, 38 each arranged for co-operation with a respective one of the levers 20, 21.

However it will be appreciated that the inclined surface of the base portion of the container could be a conical, frusto-conical or part spherical surface.

The inclined surface 37 is arranged to co-operate with the abutment surface 22 and the inclined surface 38 is arranged to co-operate with the abutment surface 23.

The abutment surface 22 is formed by an edge of a web 24 formed as part of the lever 20 and the abutment surface 23 is formed by an edge of a web 25 formed as part of the lever 21.

Each of the levers 20, 21 is pivotally connected to part of the housing 9 by a respective living hinge. In the embodiment shown each of the levers 20, 21 is pivotally connected to a respective one of the two side walls 14*a*, 14*b* by a respective living hinge 26, 27.

The fluid discharge device 8 is in most respects conventional and will only be described briefly herein.

The fluid discharge device 8 has a hollow container 30 defining a reservoir containing several doses of the fluid to be dispensed and a compression pump 29 attached to one end of the container 30.

The container 30 as shown is made from a translucent or transparent plastics material however it will be appreciate that it could be made from other translucent or transparent materials such as glass.

The container has two or more supports to allow the container to be stood up on the base portion 35 and as shown two supports 40, 41 are moulded as an integral part of the container 30. These supports are useful in that, because the base portion 35 is made up of two inclined surfaces 37, 38, it could not normally be stood up vertically. The pump 29 includes a plunger (not shown) slidingly engaged within a pump casing 34 which defines a chamber (not shown) sized to accommodate a single dose of fluid. The plunger is attached to the tubular delivery tube 31 which is arranged to extend from one end of the pump 29 for co-operation with the outlet tube 16 of the dispensing nozzle 11. The plunger includes a piston (not shown) slidably supported in the chamber formed in the pump casing 34.

The fluid is discharged through a discharge channel defined by the tubular delivery tube 31 into the orifice 15 of the dispensing nozzle 11.

The size of chamber is such that it accommodates a single dose of fluid, the diameter of the chamber and piston combined with the stroke of the plunger being such that a full stroke of the plunger in the chamber will produce a change in volume equal to a single dose of fluid.

The pump casing 34 is connected to the container 30 such that when the piston is moved by a return spring (not shown) into a start position a new dose of fluid is drawn into the cylinder via the suction inlet in the form of a pick-up tube 32 from the container 30 ready for discharge.

The tapering form of the base portion 35 of the container 30 is advantageous in that it allows the pick up tube 32 to collect, without special orientation of the container, more fluid than if a flat bottomed container is used.

The end cap 7 is a tubular component which is closed at one end and has a thin flexible side wall which defines a cavity into which the nozzle 11 is engaged to protect the nozzle 11 from damage.

It is envisaged that the end cap may be attached to the body by a flexible strap or tether which could be moulded as part of the end cap or the end cap and the body could be made as a single component.

Assembly and operation of the fluid dispensing device is as follows.

Figure 4:
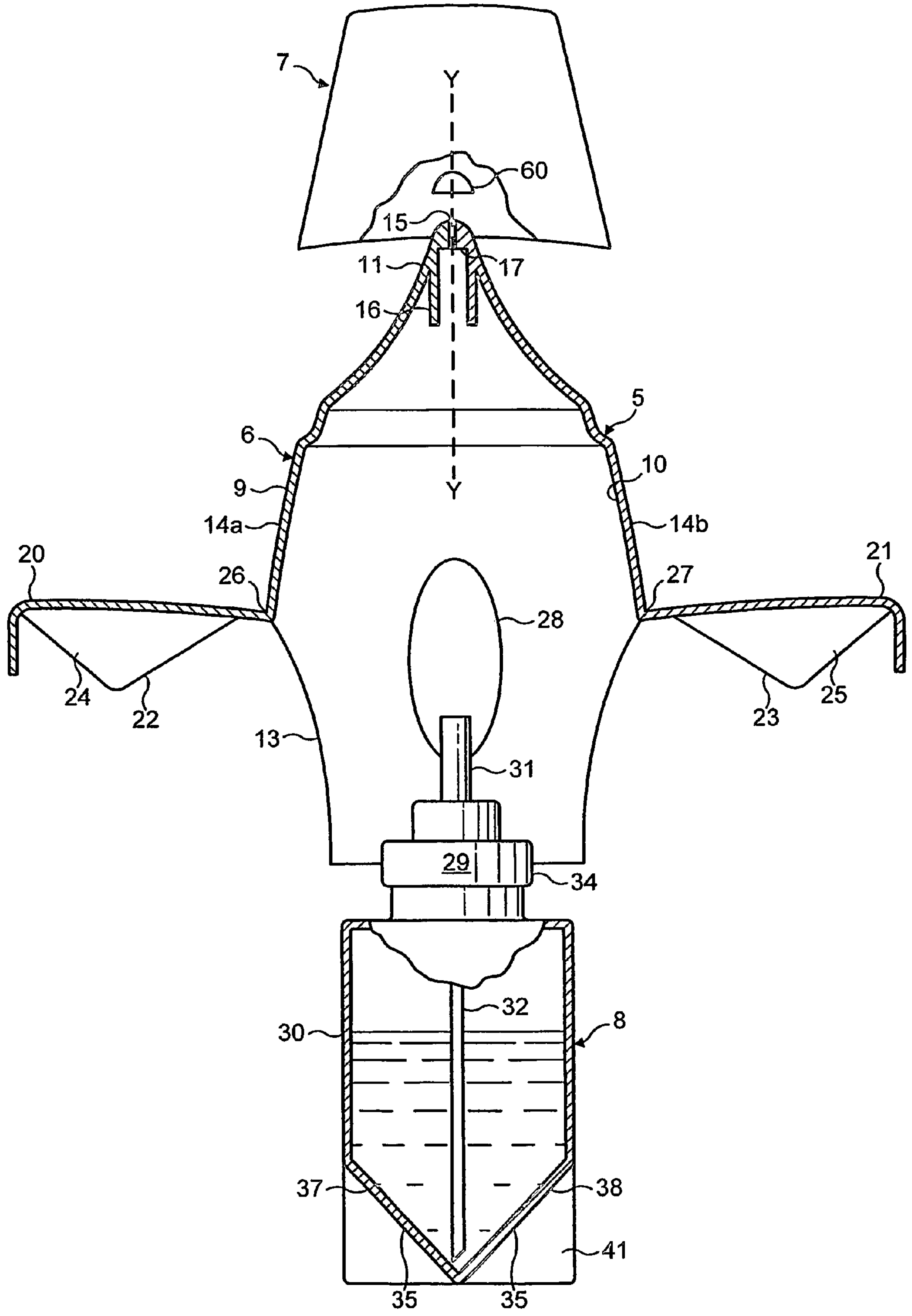
FIG. 4 is a cross-section similar to that shown in FIG. 1 but showing the insertion of a fluid discharge device according to a second aspect of the invention into a housing assembly according to a third aspect of the invention.

FIG. 4 shows the fluid dispensing device 5 in a partly assembled state in which the two levers 20, 21 have been moved into a loading position to allow the fluid discharge device 8 to be inserted into the cavity 10 in the housing 9. In the partly assembled state, the stopper end 60 has been removed from the annular abutment end 17 of the nozzle 11 to unseal the orifice 15.

From the position shown the fluid discharge device 8 is moved upwardly until the delivery tube 31 fully engages with the outlet tube 16. The two levers 20, 21 are then folded down into the position shown in FIG. 1 such that end portions of the abutment surfaces 22, 23 abut gently against the inclined surfaces 37, 38 of the container 30. The levers 20, 21 in this position are used to hold the fluid discharge device 8 within the housing 9.

If required the container 30 or the pump casing 34 could be slidably engageable with one or more support structures (not shown) to assist with the location and retention of the fluid discharge device 8 in the housing 9.

Figure 5:
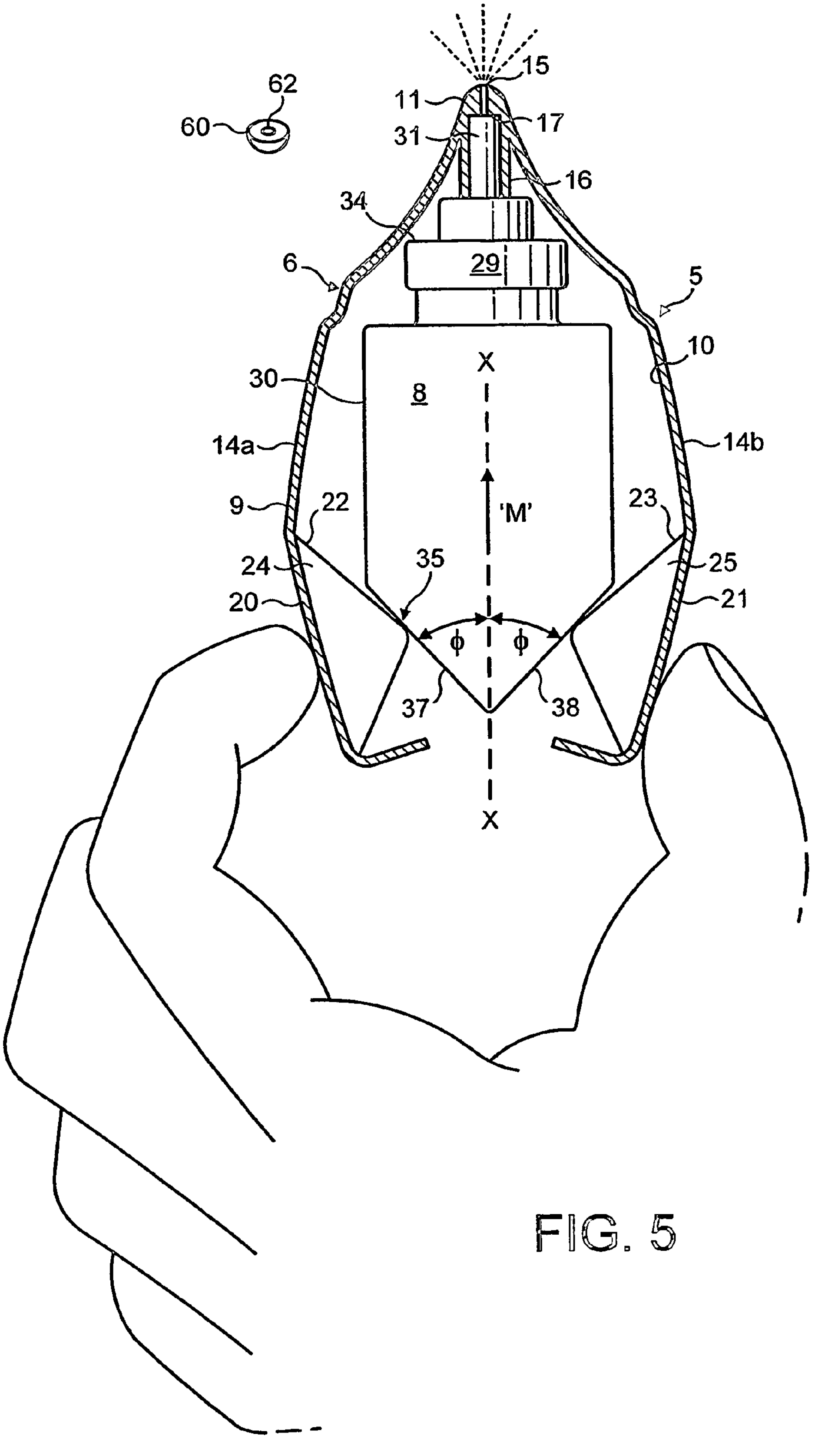
FIG. 5 is a cross-section similar to that of FIG. 1 but showing the fluid dispensing device in an use, unstoppered state.

As shown in FIG. 5, in use, the end stopper 60 is removed from the annular abutment end 17 of the nozzle 11 to unseal the orifice 15. The end stopper 60 is shown in up-ended view in which inner cavity 62 may be seen. It will be appreciated that the cavity 62 is sized and shaped for effective, snug receipt by the annular nozzle end to ensure good sealing of the orifice 15.

To enable dispensing of fluid, a user first grasps the fluid dispensing device 5 by the two levers 20, 21. Provided that only a light pressure is applied to the levers 20, 21 no fluid will be discharged and the user is able to manoeuvre the dispensing nozzle 11 of the fluid dispensing device 5 into the body orifice into which fluid is required to be dispensed. This is because of the presence of the pre-loading means.

If the user then squeezes the two levers 20, 21 together with increasing force the interaction of the abutment surfaces 22, 23 with the inclined surfaces 37, 38 causes the container 30 to be moved towards the nozzle 11 as indicated by the arrow 'M' on FIG. 5.

However, the abutment between the end of the delivery tube 31 and the annular abutment 17 will prevent movement of the delivery tube 31 in the same direction. This effect of this is to cause the delivery tube 31 to push the plunger into the pump casing 34 thereby moving the piston of the pump in the cylinder. This movement causes fluid to be expelled from the cylinder into the delivery tube 31. The fluid forced into the delivery tube is then transferred into the orifice 15 from where it is expelled as a fine spray into the body orifice.

Upon releasing the pressure applied to the levers 20, 21 the delivery tube 31 is urged out of the pump casing by the internal return spring and causes fluid to be drawn up the pick-up tube 32 to re-fill the cylinder.

The actuating procedure can then be repeated until all of the fluid in the container has been used. However, only one or two doses of fluid are normally administered at a time.

After use, the end stopper 60 will be replaced on the annular end 17 of the nozzle 11 to seal the orifice 15 and prevent drain back of fluid to the delivery tube 31.

When the container is empty a new fluid discharge device 8 is loaded into the housing 9 thereby restoring the fluid dispensing device 5 into a useable condition.

With reference to FIGS. 6 to 11 there is shown a second embodiment of a fluid dispensing device for spraying a fluid into a body cavity which is in many respects similar to that previously described.

The fluid dispensing device 105 comprising a housing 109, a nozzle 111 for insertion into a body cavity, a fluid discharge device 108 moveably housed within the housing 109, the fluid discharge device 108 comprising a container 130 for storing the fluid to be dispensed and a compression pump 129 having a suction inlet located within the container 130 and a discharge outlet for transferring fluid from the pump 129 to the nozzle 111 and finger operable means 120, 121 to apply a force to the container 130 to move the container 130 towards the nozzle 111 so as to actuate the pump 129. The finger operable means is in the form of two opposing levers 120, 121 each of which is pivotally connected to part of the housing 109 and is arranged to act upon the container 130 so as to urge the container 130 towards the nozzle 111 when the two levers 120, 121 are squeezed together by a user.

In more detail, the housing 109 comprises of a plastic cover member 110 and a plastic body member 106 both of which are moulded from a suitable plastic material such as polypropylene. It will be appreciated that the shape of the housing need not be oval it could be cylindrical or any other convenient shape.

The nozzle 111 is formed as an integral part of the body member 106 and the body member 106 is fastened within the cover member 110 so that the nozzle 111 projects from one end of the cover member 110. The outer surface or a part of the outer surface of the nozzle could be made from a soft-touch plastics material.

The cover member 110 comprises of two cover shells 118*a*, 118*b* joined together at one end by an annular ring 119.

A protective end cap 107 for the nozzle 111 is connected to the annular ring 119 such that the end cap 107, the annular ring 119 and the two cover shells 118*a*, 118*b* are made as a one piece plastic component. The protective end cap may be moulded and arranged so as to be biased to a closed position or may alternatively be biased to an open position.

The protective end cap 107 has an inner surface for engagement with the body 106 to protect the dispensing nozzle 111. Two detents 149 are provided on the inner surface of the end cap 107 to releasably hold the end cap 107 in place when it is in its protective position. The end cap 107 has a protruding stopper end 160 which has a convex, resilient end 161 form arranged for sealing engagement with a recess 141 in the end of the nozzle 111 so as provide an essentially airtight seal to nozzle orifice 115 to prevent fluid drain back when the stopper end 160 is in place.

FIG. 8*a* shows a cross-sectional view of the end cap 107 with protruding stopper end 160 having convex end 161 shaped for effective sealing.

Each of the cover shells 118*a* and 118*b* is of a semi-cylindrical shape and has two longitudinal edges 112, an end edge 113 and two transverse edges 116. At least one longitudinal edge 112 of each cover shell 118*a*, 118*b* has a recess 114 formed therein. The recesses 114 co-operate to define a window 150 through which the level of the fluid in the container 130 can be checked.

In the embodiment shown and described both longitudinal edges 112 of each cover shell 118*a*, 118*b* have a recess 114 formed therein and the recesses 114 co-operate to define two windows 150 on opposite sides of the housing 109 through which the level of the fluid in the container 130 can be checked.

Each of the cover shells 118*a*, 118*b* has an aperture 145*a*, 145*b* formed therein from which, in use, a part of a respective one of the levers 120, 121 projects. The part of each lever 120, 121 which projects from the aperture 145*a*, 145*b* is a ribbed finger grip 146 formed at the opposite end of each lever 120, 121 from where it is hingedly connected to the body member 106. A part of each lever and in particular the finger grips may be moulded from a soft touch plastic material.

As is shown in FIG. 7*a* the fluid dispensing device includes a means to prevent inadvertent movement of the two levers when not in use. The means is a portion of each cover member 118*a*, 118*b* which overlies an end portion of each lever 120, 121. More specifically, each of the cover shells 118*a*, 118*b* extends around the base portion of the cover to provide an overlying shield 200. The shields 200 act as a means to prevent inadvertent movement of the two levers 120, 121.

The advantage of this construction is that accidental operation of the dispensing device when it is carried in a bag or pocket or generally is less likely to occur because the bottom portions of the levers 120, 121 are covered and specific finger pressure has to be applied. It will be appreciated that a physical locking mechanism could also or alternatively be provided to prevent accidental movement of the two levers 120, 121.

The body member 106 is engaged with the annular ring 119 to fasten the cover member 110 to the body member 106. The body member 106 has a cylindrical portion for engagement with the annular ring 119.

Two detents 143 are formed on the cylindrical portion and two legs 144 are connected near to one end of the cylindrical portion. The detents 143 are used to trap the annular ring 119 against the legs 144 and thereby form a snap connection used to fasten the body member 106 to the cover member 110. It will be appreciated that other forms of snap fastening means could be provided.

Each of the levers 120, 121 is pivotally connected to the body member 106 by a living hinge 126, 127. The living hinges 126, 127 are formed at the juncture of the levers 120, 121 with the legs 144.

However, it will be appreciated that the levers could alternatively be pivotally connected to the cover member by a living hinge and that in either case the invention is not limited to the use of a living hinge other hinge mechanisms could be used. The discharge outlet from the pump 129 is in the form of a tubular delivery tube (not shown) and a tubular guide in the form of an outlet tube (not shown) is formed within the nozzle 111 to align and locate the delivery tube correctly with respect to the nozzle 111.

An annular abutment is formed at the end of the outlet tube. The annular abutment defines the entry to an orifice 115 through which fluid can flow in use and is arranged for abutment with an end of the delivery tube.

The fluid discharge device 108 has a longitudinal axis Z-Z and each of the levers 120, 121 has an abutment surface 122 (only one of which is visible in the Figures) arranged at an angle to the longitudinal axis Z-Z of the fluid discharge device 108 for abutment against a base portion 135 of the container so as to convert a force applied to the levers 120, 121 substantially transversely to the longitudinal axis Z-Z of the fluid discharge device 108 into a force along the longitudinal axis Z-Z of the fluid discharge device 108.

This arrangement allows a standard fluid discharge device to be used without modification.

The nozzle 111 has a longitudinal axis P-P and the longitudinal axis Z-Z of the fluid discharge device 108 is aligned with the longitudinal axis P-P of the nozzle 111. This has the advantage that when the pump 129 is actuated the force applied to the tubular delivery tube is along the axis of the tubular delivery tube and no bending or deflection of the delivery tube will occur due to the applied force.

At least part of the surface of the base portion 135 of the container 130 is inclined at an angle with respect to the longitudinal axis Z-Z of the fluid discharge device 108 so as to form an inclined surface, the or each inclined surface being arranged to be acted upon by the levers 120, 121 so as to convert a force applied to the levers 120, 121 substantially transversely to the longitudinal axis Z-Z of the fluid discharge device 108 into a force along the longitudinal axis Z-Z of the fluid discharge device 108.

Although in the disclosed embodiment both the levers and the container have surfaces inclined to the longitudinal axis of the fluid discharge device this need not be the case. Only the container or the levers need have an inclined surface or some other arrangement to apply the force from the levers to the container could be used.

In accordance with this embodiment the base portion 135 of the container has a conical inclined surface 138 arranged for co-operation with the levers 120, 121.

However, it will be appreciated that the inclined surface of the base portion of the container could be a frusto-conical or part spherical surface or could be comprised of two separate inclined surfaces each for co-operation with a respective one of the levers.

The inclined surface 138 is arranged to co-operate with both abutment surfaces 122 of the levers 120, 121.

The fluid discharge device 108 is in most respects conventional and will only be described briefly herein.

The fluid discharge device 108 has a hollow container 130 defining a reservoir containing several doses of the fluid to be dispensed and a compression pump 129 attached to one end of the container 130.

The container 130 as shown is made from glass however it will be appreciated that it could be made from other translucent or transparent materials such as plastic. The pump 129 includes a plunger (not shown) slidingly engaged within a pump casing 134 which defines a chamber (not shown) sized to accommodate a single dose of fluid. The plunger is attached to the tubular delivery tube which is arranged to extend from one end of the pump 129 for co-operation with the outlet tube of the dispensing nozzle 111. The plunger includes a piston (not shown) slidably supported in the chamber formed in the pump casing 134.

The fluid is discharged through a discharge channel defined by the tubular delivery tube into the orifice 115 of the dispensing nozzle 111.

The size of chamber is such that it accommodates a single dose of fluid, the diameter of the chamber and piston combined with the stroke of the plunger being such that a full stroke of the plunger in the chamber will produce a change in volume equal to a single dose of fluid.

The pump casing 134 is connected to the container 130 such that when the piston is moved by an internal return spring (not shown) into a start position a new dose of fluid is drawn into the cylinder via the suction inlet in the form of a pick-up tube from the container 130 ready for discharge.

The conical form of the base portion 135 of the container 130 is particularly advantageous in that it allows the pick up tube to collect more fluid, without special orientation of the container, than if a flat bottomed container is used.

Assembly and operation of the fluid dispensing device is as follows.

The first stage of assembly is to position the levers 120, 121 in the position shown in FIG. 9 and then insert the fluid discharge device 108 into the body member 106.

This is done by engaging the pump casing 134 with a cylindrical bore in the cylindrical portion of the body member 106 and engaging the delivery tube with the outlet tube such that an end of the delivery tube is in abutment with the annular abutment in the outlet tube. The engagement of the pump casing 134 with the cylindrical portion of the body member 106 is such that the pump casing 134 is able to slide in the cylindrical bore when a force is applied to the container 130 but is gripped sufficiently to hold the fluid discharge device 108 in position.

FIG. 11 shows the fluid dispensing device 105 in a partly assembled state after this initial assembly operation in which the fluid discharge device 108 has been inserted into the body member 106. The two levers 120, 121 have been folded down from the position shown in FIG. 9 into a ready for use position such that end portions of the abutment surfaces 122 and in particular the ridges 170 are positioned adjacent to a side wall of the container and near to the inclined conical surface 138 of the container 130.

To complete the assembly of the fluid dispensing device 105 the cylindrical portion of the body member 106 is inserted into the annular ring 119 and the two parts are snapped together. The two cover shells 118*a* and 118*b* are then folded down from the position shown in FIG. 10 into the position shown in FIG. 6.

It will be appreciated that in the fully assembled state the stopper end 160 of the end cap 107 is sealingly received by the recess 141 in the end of the nozzle 111 thereby providing an essentially airtight seal to nozzle orifice 115 to prevent fluid drain back when the stopper end 160 is in place.

Figure 6:
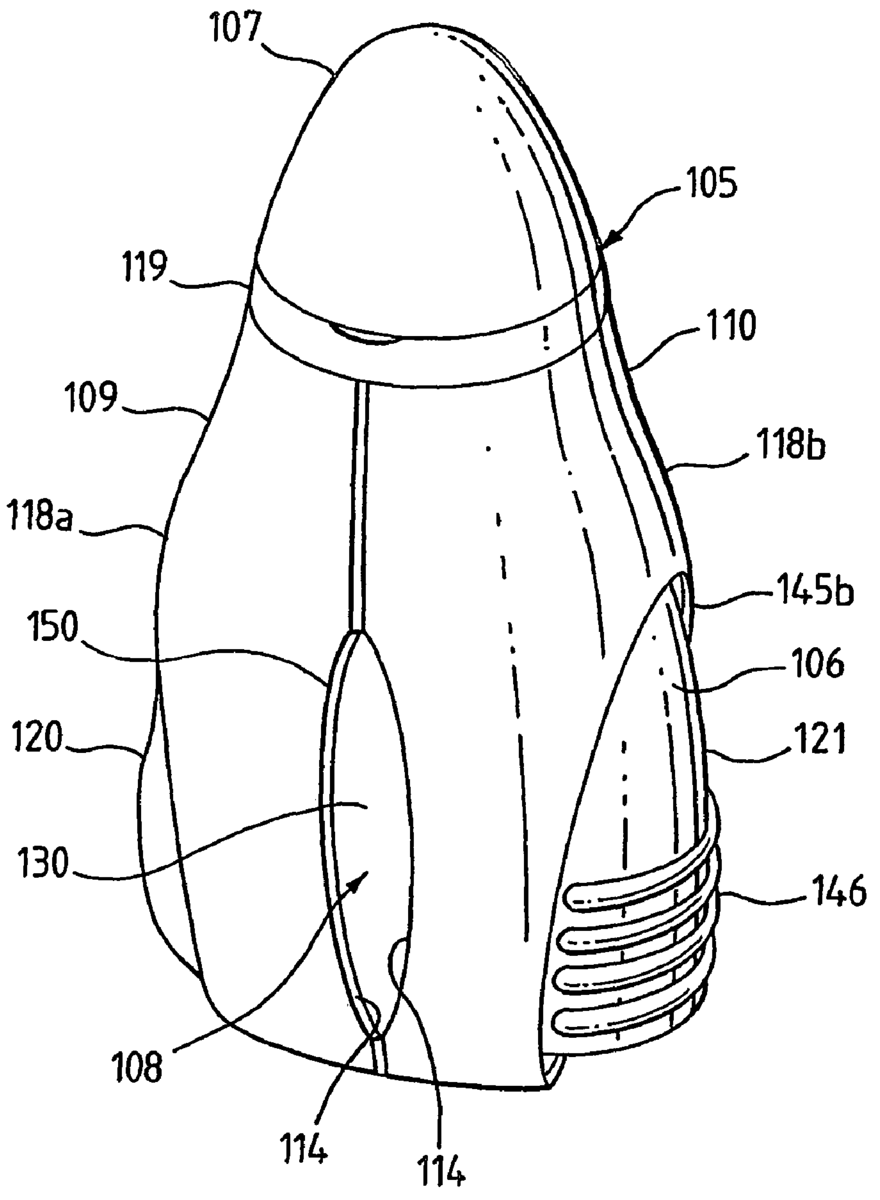
FIG. 6 is a pictorial representation as viewed from a front right hand corner of a second embodiment of a fluid dispensing device according to the invention in a stored state with a protective end cap in place.

The abutting transverse edges 116 of the two cover shells 118*a* and 118*b* include complementary detents (not shown) such that when the cover shells 118*a*, 118*b* are pushed together the detents snap together to hold them in the position shown in FIGS. 6 and 7. As an additional measure an adhesive backed label (not shown) can be applied across the joint between the two cover shells 118*a* and 118*b* on the base on the assembled fluid dispensing device 105 to prevent the cover shells 118*a*, 118*b* from accidentally snapping open but more importantly to provide an indication that the fluid dispensing device 105 has not been tampered with.

To use the fluid dispensing device 105 a user first has to remove the protective cap 107 (as shown in FIG. 7) thereby unsealing the nozzle orifice 115 by removing the stopper end 160 from the nozzle recess 141. The user then grasps the fluid dispensing device 105 by the two levers 120, 121 and in particular by the two ribbed finger grips 146.

Provided that only a light pressure is applied to the levers 120, 121 no fluid will be discharged and the user is able to manoeuvre the dispensing nozzle 111 of the fluid dispensing device 105 into a body orifice such as a nasal cavity into which fluid is required to be dispensed.

If the user then squeezes the two levers 120, 121 together with increasing force the interaction of the abutment surfaces 122 upon the inclined conical surface 138 will then cause the container 130 to be moved rapidly towards the nozzle 111.

However, because of the abutment between the end of the delivery tube and the annular abutment movement of the delivery tube in the same direction is prevented and therefore the delivery tube acts so as to push the plunger into the pump casing 134 thereby moving the piston of the pump in the cylinder. This causes fluid to be expelled from the cylinder into the delivery tube and then into the orifice 115 from where it is expelled as a fine spray into the body orifice.

Upon releasing the pressure applied to the levers 120, 121 the delivery tube is urged out of the pump casing by the internal return spring and causes fluid to be drawn up the pick-up tube to re-fill the cylinder.

The actuating procedure can then be repeated until all of the fluid in the container has been used. However, only one or two doses of fluid are normally administered at a time.

When the container 130 is empty a new fluid discharge device 108 is loaded into the body member 106 thereby restoring the fluid dispensing device 105 into a useable condition.

With reference to FIG. 12 there is shown (in part cut-away form) a third embodiment of a fluid dispensing device for spraying a fluid into a body cavity.

The fluid dispensing device 205 comprises a housing 209, a nozzle 211 for insertion into a body cavity, a fluid discharge device 208 moveably housed within the housing 209, the fluid discharge device 208 (of generally conventional form, as described previously) comprising a container 230 for storing the fluid to be dispensed and a compression pump 229 having a suction inlet located within the container 230 and a discharge outlet for transferring fluid from the pump 229 to the nozzle 211.

The discharge outlet from the pump 229 is in the form of a tubular delivery tube 231 and a tubular guide in the form of an outlet tube 216 is formed within the nozzle 211 to align and locate the delivery tube 231 correctly with respect to the nozzle 211.

An annular abutment 217 is formed at the end of the outlet tube 216. The annular abutment 217 defines the entry to the outlet tube 216 through which in use, fluid can be delivered to the nozzle orifice and is arranged for abutment with a circular lip 232 of the pump 229.

The housing 209 comprises body member 206 moulded from a suitable plastic material such as polypropylene. It will be appreciated that the shape of the housing need not be oval it could be cylindrical or any other convenient shape. The nozzle 211 is formed as an integral part of the body member 206. The outer surface or a part of the outer surface of the nozzle could be made from a soft-touch plastics material.

The device 205 is provided with a protective end cap 207 having an inner surface for engagement with the body 206 to protect the dispensing nozzle 211. The end cap 207 is pivotally mounted to the body 206 at pivot-point 252. Detent 249 is provided to the inner surface of the end cap 207 to releasably hold the end cap 207 in place when it is in its protective position. The inner surface of end cap 207 is further provided with annular, protruding walls 264 for housing resilient stopper 260 (e.g. formed of rubber). When the end cap 207 is in the storage position (as shown in FIG. 12) the stopper 260 sealingly engages the concave tip 213 of nozzle 211 such as provide an essentially airtight seal to nozzle orifice 215 to prevent fluid drain back down outlet tube 216 when the stopper end 260 is in place.

FIGS. 13*a* to 13*c* show simplified representations of various end cap/stopper configurations suitable for use with any of the fluid dispensing devices described herein.

In each of the variations of FIGS. 13*a* to 13*c*, fluid dispensing device 305 comprises a body 306 including a nozzle 311 formed as an integral part thereof. The body 306 has a plastic end cap 307 mounted thereto.

In the variation of FIG. 13*a*, the end cap 307 is reversibly push mounted onto the body 306.

In the variation of FIG. 13*b*, the end cap 307 joins to the body 306 at living hinge point 352 such that the end cap 307 is hingedly moveable from a storage position in which the end cap 307 covers the nozzle 311 to an in-use position in which the nozzle 311 is uncovered. Detent 349 is provided to the inner surface of the end cap 307 to releasably hold the end cap 307 in place when it is in its storage position.

In the variation of FIG. 13*c*, the end cap 307 is snap-fit mounted to the body 306 352 such that the end cap 307 is hingedly moveable from a storage position in which the end cap 307 covers the nozzle 311 to an in-use position in which the nozzle 311 is uncovered. Annular ring retainer 349 is provided to the inner surface of the end cap 307 for engagement with the annular upper lip 355 of the body 306 to releasably hold the end cap 307 in place when it is in its storage position.

In each of the variations of FIGS. 13*a* to 13*c*, the body 306 and end cap 307 are suitably moulded from a suitable plastic material such as polypropylene. The outer surface or a part of the outer surface of the nozzle 311 could be made from a soft-touch plastics material. The inner surface of end cap 307 is further provided with annular, protruding walls 364 for housing resilient stopper 360 (e.g. formed of rubber). When the end cap 307 is in the storage position (as shown in each of FIGS. 13*a* to 13*c*) the stopper 360 sealingly engages the concave tip 313 of nozzle 311 such as provide an essentially airtight seal to nozzle orifice 315 to prevent fluid drain back when the stopper end 360 is in place.

Suitable stoppers 260, 360 shaped for retention within an inner wall 264, 364 structure of a protective end cap 207, 307 (e.g. as shown in FIGS. 12 to 13*c*) may be formed in a variety of ways. In one aspect, a rubber disc-shaped stopper is stamped from a sheet of rubber. In another aspect, a disc-shaped stopper is moulded (e.g. by an injection moulding process). In a further aspect, the protective end cap is moulded and the stopper is then moulded within the formed end cap (i.e. a 'two shot' moulding process).

Other variations of stopper and end cap are shown in FIGS. 14*a* to 22, in which only a top part of the nozzle end of the dispensing device is shown. It will be appreciated that each of these variations may be incorporated as alternatives in the dispensing devices already illustrated and described.

In more detail, the stopper 460 of FIGS. 14*a* and 14*b* has a 'bowler hat' form and comprises disc-shaped base 466 and hemispherical head 465 formed of a resiliently compressible material. The end cap 407 for the dispensing orifice 415 of the nozzle 411 is further provided at its inner surface with annular, protruding walls 464 for housing resilient stopper 460 in 'bowler hat' configuration. When the end cap 407 is in the storage position (as shown in FIG. 14*a*) the base 466 of the stopper 460 sealingly engages the dispensing orifice 415 at the tip 413 of nozzle 411 such as provide an essentially airtight seal to the dispensing orifice 415 to prevent fluid drain back when the stopper end 460 is in place. In embodiments, either a chordal section is cut away from the base 466 of the stopper or the base 466 is formed with such a 'cut away' shape thereby providing a base 466 shaped to assist with ready insertion of the stopper 460 into the annual protruding walls 464.

The stopper 560 of FIG. 15 is in the form of a 'thin wall' part of end cap 507. In more detail, the end cap 507 for the dispensing orifice 515 of the nozzle 511 is provided at its inner surface with annular, protruding walls 564 supporting a relatively flexible, thin wall 560, which in use, functions as a stopper 560. When the end cap 507 is in the storage position (as shown in FIG. 15) the lower surface of the thin wall stopper 560 sealingly engages the dispensing orifice 515 at the tip 513 of nozzle 511 such as provide an essentially airtight seal to the dispensing orifice 515 to prevent fluid drain back when the thin wall stopper 560 part of the end cap 507 is in place. A plug insert 570 is also provided to plug the cavity 572 defined by the annular, protruding walls 564 of the end cap and thereby to protect the thin wall stopper 560 from damage.

The stopper 660 of FIG. 16 is a variation of that of FIG. 15. In more detail, stopper 660 of FIG. 16 is in the form of a compressible 'thin walled' part of end cap 607. In more detail, the end cap 607 for the dispensing orifice 615 of the nozzle 611 is provided at its inner surface with compressible, protruding annular walls 664 supporting a flexible, thin wall 660, which in use, functions as a stopper 660. When the end cap 607 is in the storage position (as shown in FIG. 16) the lower surface of the thin wall stopper 660 sealingly engages the dispensing orifice 613 at the tip 615 of nozzle 611 such as provide an essentially airtight seal to the dispensing orifice 615 to prevent fluid drain back when the thin wall stopper 660 part of the end cap 607 is in place. The annular walls 664 are part-compressed when the stopper 660 sealingly interacts with the tip 613 of the nozzle 611. A plug insert 670 is also provided to plug the cavity 672 defined by the compressible annular, protruding walls 664 of the end cap and thereby to protect the thin wall stopper 660 from damage.

In turn, the stopper 760 of FIG. 17 is a variation of that of FIG. 16. In more detail, stopper 760 of FIG. 16 is in the form of a compressible 'thin walled' concertina part 761 provided to end cap 707. In more detail, the end cap 707 for the dispensing orifice 715 of the nozzle 711 is provided at its inner surface with compressible, protruding annular walls 764 supporting a concertina part 761 which at its end has a flexible, thin wall 760 that in use, functions as a stopper 760. When the end cap 707 is in the storage position (as shown in FIG. 17) the lower surface of the thin wall stopper 760 sealingly engages the dispensing orifice 713 at the tip 715 of nozzle 711 such as provide an essentially airtight seal to the dispensing orifice 715 to prevent fluid drain back when the thin wall stopper 760 part of the end cap 707 is in place. The concertina part 761 is part-compressed when the stopper 760 sealingly interacts with the tip 713 of the nozzle 711.

FIGS. 18 and 19 both illustrate end caps with stoppers that are susceptible to manufacture by 'two shot moulding' operations.

In more detail, the stopper 860 of FIG. 18 is formed of a resiliently compressible material applied as a 'second shot' moulding to an end cap 807 previously formed by a first moulding operation. The end cap 807 for the dispensing orifice 815 of the nozzle 811 is provided at its inner surface with annular, protruding walls 864 that in part, define the shape of resilient stopper 860. When the end cap 807 is in the storage position (as shown in FIG. 18) the base 866 of the stopper 860 sealingly engages the dispensing orifice 815 at the tip 813 of nozzle 811 such as provide an essentially airtight seal to the dispensing orifice 815 to prevent fluid drain back when the stopper 860 is in place.

The stopper 960 of FIG. 19 is also formed of a resiliently compressible material applied as a 'second shot' moulding to an end cap 907 previously formed by a first moulding operation, but the amount of material provided during the 'second shot' moulding operation is more extensive. In more detail, the end cap 907 for the dispensing orifice 915 of the nozzle 911 is provided at its inner surface with annular, protruding walls 964 that in part, define the shape of the moulding which forms resilient stopper 960. That moulding also however, extends down part of the inner surface (right hand side, as shown) of the end cap 907 to form a hinge 980 attachment means that connects to the base 919 of nozzle 911 at attachment point 982. It will therefore be appreciated that the end cap 907 is both attached to the nozzle 911 and hingedly moveable about hinge 980 from a storage position (nozzle 911 covered) to an in-use position (nozzle 911 uncovered). When the end 907 is in the storage position (as shown in FIG. 19) the base 966 of the stopper 960 sealingly engages the dispensing orifice 915 at the tip 913 of nozzle 911 such as provide an essentially airtight seal to the dispensing orifice 915 to prevent fluid drain back when the stopper 960 is in place.

Stopper 1060 of FIG. 20 may be seen to form an integral part of end cap 1007. Dispensing nozzle 1011 is provided at its tip 1013 with a head 1016 of relatively soft and compressible material in the form of a ring defining a channel 1017 shaped for receipt of the base 1066 of the stopper 1060. When the end cap 1007 is in the storage position the base 1066 of the stopper 1060 inserts into the channel 1017 defined by the soft ring 1016 at the nozzle tip 1015 and sealingly engages the dispensing orifice 1015 at the tip 1013 of nozzle 1011 such as provide an essentially airtight seal to the dispensing orifice 1015 to prevent fluid drain back.

Stopper 1160 of FIG. 21 has 'roller ball' form. In more detail, end cap 1107 for the dispensing orifice 1115 of the nozzle 1111 is further provided at its inner surface with annular, protruding walls 1164 provided with skirt 1165 for receipt by groove 1168 provided to the roller ball form resilient stopper 1160 such as to retain the stopper 1160. When the end cap 1107 is in the storage position (as shown in FIG. 21) the spherical base 1166 of the stopper 1160 sealingly engages the dispensing orifice 1113 at the tip 1115 of nozzle 1111 such as provide an essentially airtight seal to the dispensing orifice 1115 to prevent fluid drain back when the stopper 1160 is in place.

Stopper 1260 of FIG. 22 has a 'concave hollow' form and comprises resiliently compressible material. In more detail, the end cap 1207 for the dispensing orifice 1215 of the nozzle 1211 is provided at its inner surface with annular, protruding walls 1264 for housing resilient stopper 1260 as shown. When the end cap 1207 is in the storage position (as shown in FIG. 22) the concave base 1266 of the stopper 1260 sealingly engages the dispensing orifice 1213 at the convex tip 1215 of nozzle 1211 such as provide an essentially airtight seal to the dispensing orifice 1215 to prevent fluid drain back when the stopper 1260 is in place. The end cap 1207 is also provided with hinge attachment means 1280 for hinged attachment to the body of a dispensing device (not shown).

FIG. 23 shows a simplified representation of an alternative end cap suitable for use with any of the fluid dispensing devices described herein, in which fluid dispensing device 1305 comprises a body 1306 including a nozzle 1311 formed as an integral part thereof. The body 1306 has a plastic end cap 1307 mounted thereto. The end cap 1307 is reversibly push mounted onto the body 1306.

The body 1306 and end cap 1307 are suitably moulded from a plastic material such as polypropylene. The outer surface or a part of the outer surface of the nozzle 1311 could be made from a soft-touch plastics material. The inner surface of end cap 1307 is further provided with an annular, protruding wall 1364 having a flexible rim 1365 shaped for interference engagement in the storage position (as shown in FIG. 23) with the nozzle 1311 to thereby define a sealed cavity space 1360. In the storage position, the sealed cavity space 1360 acts by way of a 'reverse pressure effect' to prevent fluid drain back at the nozzle orifice 1315.

It will be appreciated that the embodiment of FIG. 23 uses a 'sealed cavity space' adjacent to the dispensing orifice 1315 to prevent drain back as alternative to the use of a stopper seal. It can however, be difficult to ensure the integrity of this 'sealed cavity space', which difficulty does not arise with the stopper approach.

With reference to FIGS. 24*a* to 24*e* there is shown a further embodiment of a fluid dispensing device for spraying a fluid into a body cavity, which is in many respects similar to that previously described.

The fluid dispensing device 1405 comprising a housing 1409, a nozzle 1411 for insertion into a body cavity, a fluid discharge device 1408 moveably housed within the housing

1409, the fluid discharge device 1408 comprising a container 1430 for storing the fluid to be dispensed and a compression pump 1429 having a suction inlet located within the container 1430 and a discharge outlet for transferring fluid from the pump 1429 to the nozzle 1411 and finger operable means 1420 to apply a force to the container 1430 to move the container 1430 towards the nozzle 1411 so as to actuate the pump 1429. The finger operable means is in the form of a lever 1420 pivotally connected to part of the housing 1409 and arranged to act upon the container 1430 so as to urge the container 1430 towards the nozzle 1411 when lever 1420 is squeezed inwardly by a user. The body 1409 is also provided with a window 1450 through which the level of the fluid in the container 1430 can be checked.

The nozzle 1411 is formed as an integral part of the body member 1406 and the body member 1406 is provided with a protective end cap 1407 for protection of the nozzle 1411. The outer surface or a part of the outer surface of the nozzle could be made from a soft-touch plastics material. First and second lugs 1449*a*, 1449*b* project from the protective end cap 1407 for receipt within suitably arranged channels provided within the body 1406 such as to allow secure attachment of the end cap 1407 to the body 1406. When so-received, first lug 1449*a* further interferes with movement of lever 1420 such as to prevent actuation (i.e. to lock movement) of the lever 1420 when the end cap 1407 and lugs 1449*a*, 1449*b* are in place (i.e. in the nozzle covered position).

The end cap 1407 also has a protruding stopper 1460 which has a convex, resilient end 1461 form arranged for sealing engagement with the dispensing orifice 1415 of the nozzle 1411 so as provide an essentially airtight seal to nozzle orifice 1415 to prevent fluid drain back when the stopper 1460 is in place.

The fluid discharge device 1408 has a longitudinal axis Z-Z and the lever 1420, has a guide surface in the form of a beak 1422 arranged for interaction with a drive dog 1492 provided to a collar 1490 fixed around the neck of the container 1430. It will be appreciated that sideways force (i.e. substantially transversely to the longitudinal axis Z-Z of the fluid discharge device 1408) applied to the lever 1420 results in movement of the dog 1492 along the guide surface defined by the beak 1422 thereby resulting in upward movement (i.e. along the longitudinal axis Z-Z) of the fluid discharge device 1408.

In a subtle aspect, the ramp form guide surface 1422 has a variable mechanical ratio arranged such that until a pre-determined force is applied to the lever 1420 no significant force is transferred to the container 1430.

In more detail, a first portion 1423*a* of the ramp 1422 is inclined at a lesser angle (e.g. approx 20°) to a longitudinal (i.e. vertical, as shown) axis of the fluid discharge device 1408 than is the remaining length 1423*b* (e.g. angle approx. 45°) of the beak 1422. Therefore when a force is initially applied to the lever 1420 it is applied substantially normal to the longitudinal axis of the fluid discharge device 1408 and virtually no force is converted into a force along the longitudinal axis of the fluid discharge device 1408 and so the static friction between the first portion 1423*a* of the beak 1422 and the drive dog 1492 is sufficient to maintain the lever 1420, stationary. However, when a pre-determined load is applied to the lever 1420 the static friction is overcome and the dog 1492 is able to start moving along the first portion 1423*a* of the cooperating beak 1422. When the dog 1492 reaches the end of the first portion 1423*a*, the change in inclination of the surface with which the dog 1492 is cooperating in combination with the magnitude of the force being applied ensures that the dog 1490 suddenly slides rapidly along the second portion 1423*b* of the cooperating beak 1422 causing the container 1430 to be moved rapidly towards the nozzle 1411 to actuate the compression pump.

This ensures that the pump is only actuated when sufficient force is being applied to guarantee the production of an effective spray.

To use the fluid dispensing device 1405 of FIGS. 24*a* to 24*e* a user first has to remove the protective cap 1407 thereby unsealing the nozzle orifice 1415 by removing the stopper end 1460 therefrom. The user then grasps the fluid dispensing device 1405 and places a thumb on lever 1420.

Provided that only a light pressure is applied to the lever 1420 no fluid will be discharged and the user is able to manoeuvre the dispensing nozzle 1411 of the fluid dispensing device 1405 into a body orifice such as a nasal cavity into which fluid is required to be dispensed.

If the user then squeezes the levers 1420 inwards with increasing force the threshold force defined by the interaction of dog 1492 with first part of guide surface 1423*a* of the beak 1422 is overcome resulting in the container 1430 being moved rapidly towards the nozzle 1411 to actuate the pump 1429 and dispense fluid to the dispensing orifice 1415. Upon release of the pressure applied to the lever 1420 the pump is reset by its internal return spring.

A fluid dispensing apparatus for housing a fluid discharging device forming a second aspect of the invention is also disclosed. The fluid dispensing apparatus is in all respects the same as the fluid dispensing device previously described with the exception that it does not contain a fluid discharging device.

The fluid discharging apparatus therefore comprises of a body defining a cavity; and a dispensing nozzle having a dispensing orifice, wherein the dispensing orifice of the dispensing nozzle is provided with a reversibly mounted stopper, wherein, in use, a fluid discharging device (e.g. pump action fluid dispenser) is positioned within the cavity for co-operation the dispensing nozzle.

In aspects, the fluid dispensing apparatus further comprises an end cap for engagement with the body, the end cap being adapted to comprise a stopper, as described previously.

It is envisaged that the fluid discharging apparatus could be sold as an item into which a fluid discharging device is fitted by a user or pharmacist.

Administration of medicament may be indicated for the treatment of mild, moderate or severe acute or chronic symptoms or for prophylactic treatment. It will be appreciated that the precise dose administered will depend on the age and condition of the patient, the particular medicament used and the frequency of administration and will ultimately be at the discretion of the attendant physician. When combinations of medicaments are employed the dose of each component of the combination will in general be that employed for each component when used alone.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (eg as the sodium salt), ketotifen or nedocromil (eg as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone (eg as the furoate ester), ciclesonide, triamcinolone (eg as the acetonide), 6α,9α-difluoro-11β-hydroxy-16α-methyl-3-oxo-17α-propionyloxy-androsta-1,4-diene-17β-carbothioic acid S-(2-oxo-tetrahydro-furan-3-yl)ester or 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; PDE4 inhibitors eg cilomilast or roflumilast; leukotriene antagonists eg montelukast, pranlukast and zafirlukast; [adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]*; [α4 integrin inhibitors eg (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g as free acid or potassium salt)]*, diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is an anti-inflammatory compound for the treatment of inflammatory disorders or diseases such as asthma and rhinitis.

In one aspect, the medicament is a glucocorticoid compound, which has anti-inflammatory properties. One suitable glucocorticoid compound has the chemical name: 6α,9α-Difluoro-17α-(1-oxopropoxy)-11β-hydroxy-16α-methyl-3-oxo-androsta-1,4-diene-17β-carbothioic acid S-fluoromethyl ester (fluticasone propionate). Another suitable glucocorticoid compound has the chemical name: 6α, 9α-difluoro-17α-[(2-furanylcarbonyl)oxy]-11β-hydroxy-16α-methyl-3-oxo-androsta-1,4-diene-17β-carbothioic acid S-fluoromethyl ester. A further suitable glucocorticoid compound has the chemical name: 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

The medicament is formulated as any suitable fluid formulation, particularly a solution (e.g. aqueous) formulation or a suspension formulation, optionally containing other pharmaceutically acceptable additive components.

Suitably, the fluid medicament formulation herein has a viscosity of from 10 to 2000 mPa·s (10 to 2000 centipoise), particularly from 20 to 1000 mPa·s (20 to 1000 centipoise), such as from 50 to 1000 mPa·s (50 to 1000 centipoise) at 25° C.

Suitable formulations (e.g. solution or suspension) may be stabilised (e.g. using hydrochloric acid or sodium hydroxide) by appropriate selection of pH. Typically, the pH will be adjusted to between 4.5 and 7.5, preferably between 5.0 and 7.0, especially around 6 to 6.5.

Suitable formulations (e.g. solution or suspension) may comprise one or more excipients. By the term "excipient", herein, is meant substantially inert materials that are nontoxic and do not interact with other components of a composition in a deleterious manner including, but not limited to, pharmaceutical grades of carbohydrates, organic and inorganic salts, polymers, amino acids, phospholipids, wetting agents, emulsifiers, surfactants, poloxamers, pluronics, and ion exchange resins, and combinations thereof.

Suitable carbohydrates include monosaccharides include fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof.

Suitable organic and inorganic salts include sodium or calcium phosphates, magnesium stearate, and combinations and derivatives thereof.

Suitable polymers include natural biodegradable protein polymers, including, but not limited to, gelatin and combinations and derivatives thereof; natural biodegradable polysaccharide polymers, including, but not limited to, chitin and starch, crosslinked starch and combinations and derivatives thereof; semisynthetic biodegradable polymers, including, but not limited to, derivatives of chitosan; and synthetic biodegradable polymers, including, but not limited to, polyethylene glycols (PEG), polylactic acid (PLA), synthetic polymers including but not limited to polyvinyl alcohol and combinations and derivatives thereof;

Suitable amino acids include non-polar amino acids, such as leucine and combinations and derivatives thereof. Suitable phospholipids include lecithins and combinations and derivatives thereof.

Suitable wetting agents, surfactants and/or emulsifiers include gum acacia, cholesterol, fatty acids including combinations and derivatives thereof. Suitable poloxamers and/or Pluronics include poloxamer 188, Pluronic® F-108, and combinations and derivations thereof. Suitable ion exchange resins include amberlite IR120 and combinations and derivatives thereof; Suitable solution formulations may comprise a solubilising agent such as a surfactant. Suitable surfactants include α-[4-(1,1,3,3-tetramethylbutyl)phenyl]-ω-hydroxy-poly(oxy-1,2-ethanediyl) polymers including those of the Triton series e.g. Triton X-100, Triton X-114 and Triton X-305 in which the X number is broadly indicative of the average number of ethoxy repeating units in the polymer (typically around 7-70, particularly around 7-30 especially around 7-10) and 4-(1,1,3,3-tetramethylbutyl)phenol polymers with formaldehyde and oxirane such as those having a relative molecular weight of 3500-5000 especially 4000-4700, particularly Tyloxapol. The surfactant is typically employed in a concentration of around 0.5-10%, preferably around 2-5% w/w based on weight of formulation.

Suitable solution formulations may also comprise hydroxyl containing organic co-solvating agents include glycols such as polyethylene glycols (eg PEG 200) and propylene glycol; sugars such as dextrose; and ethanol. Dextrose and polyethylene glycol (eg PEG 200) are preferred, particularly dextrose. Propylene glycol is preferably used in an amount of no more than 20%, especially no more than 10% and is most preferably avoided altogether. Ethanol is preferably avoided. The hydroxyl containing organic co-solvating agents are typically employed at a concentration of 0.1-20% e.g. 0.5-10%, e.g. around 1-5% w/w based on weight of formulation.

Suitable solution formulations may also comprise solublising agents such as polysorbate, glycerine, benzyl alcohol, polyoxyethylene castor oils derivatives, polyethylene glycol and polyoxyethylene alkyl ethers (e.g. Cremophors, Brij).

Suitable solution formulations may also comprise one or more of the following components: viscosity enhancing agents; preservatives; and isotonicity adjusting agents.

Suitable viscosity enhancing agents include carboxymethylcellulose, veegum, tragacanth, bentonite, hydroxypropylmethylcellulose, hydroxypropylcellulose, hydroxyethylcellulose, poloxamers (eg. poloxamer 407), polyethylene glycols, alginates xanthym gums, carageenans and carbopols.

Suitable preservatives include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin.

Suitable isotonicity adjusting agents act such as to achieve isotonicity with body fluids (e.g. fluids of the nasal cavity), resulting in reduced levels of irritancy associated with many nasal formulations. Examples of suitable isotonicity adjusting agents are sodium chloride, dextrose and calcium chloride.

Suitable suspension formulations comprise an aqueous suspension of particulate medicament and optionally suspending agents, preservatives, wetting agents or isotonicity adjusting agents.

The particulate medicament suitably has a mass mean diameter (MMD) of less than 20 μm, preferably between 0.5-10 μm, especially between 1-5 μm. If particle size reduction is necessary, this may be achieved by techniques such as micronisation and/or microfluidisation.

Suitable suspending agents include carboxymethylcellulose, veegum, tragacanth, bentonite, methylcellulose and polyethylene glycols.

Suitable wetting agents function to wet the particles of medicament to facilitate dispersion thereof in the aqueous phase of the composition. Examples of wetting agents that can be used are fatty alcohols, esters and ethers. Preferably, the wetting agent is a hydrophilic, non-ionic surfactant, most preferably polyoxyethylene (20) sorbitan monooleate (supplied as the branded product Polysorbate 80).

Suitable preservatives and isotonicity adjusting agents are as described above in relation to solution formulations.

The dispensing device herein is suitable for dispensing fluid medicament formulations for the treatment of inflammatory and/or allergic conditions of the nasal passages such as rhinitis e.g. seasonal and perennial rhinitis as well as other local inflammatory conditions such as asthma, COPD and dermatitis.

A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 μg, 50 μg, 100 μg, 200 μg or 250 μg of active medicament. The precise dosage is either known or readily ascertainable by those skilled in the art.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A fluid dispensing apparatus for housing a fluid discharging device, the fluid dispensing apparatus comprising a body defining a cavity, and a dispensing nozzle having a dispensing orifice, and a protective end cap having:

an inner surface for engagement with the body, and an inner part provided with an annular wall defining a cavity in which a stopper is received as an insert thereto, wherein the stopper insert comprises a flat base and a convex head and said flat base is shaped for receipt by said cavity such that the convex head faces outwards, wherein the end cap is moveable from a first position in which it covers the nozzle to a second position in which the nozzle is uncovered, and wherein the stopper is located on the end cap such that when the end cap is in the first position the convex head of the stopper contacts the dispensing nozzle to seal the dispensing nozzle orifice and in the second position the stopper is spaced from the dispensing nozzle, and said fluid discharging device housed in the cavity of said body of said fluid dispensing apparatus, the fluid discharging device having a hollow casing defining a reservoir for containing a volume of fluid and a pump having a suction inlet extending within the hollow casing, the pump having a discharge outlet extending from a first end of the hollow casing for co-operation with the dispensing nozzle to enable pumped delivery of fluid from the reservoir to the dispensing nozzle.

2. A fluid dispensing apparatus according to claim 1, wherein the dispensing nozzle has a tip which defines a well circumferential to the dispensing orifice.

3. A fluid dispensing apparatus according to claim 1, wherein the shape of the stopper inversely mirrors that of the dispensing nozzle tip.

4. A fluid dispensing apparatus according to claim 1, wherein the stopper comprises plastic material.

5. A fluid dispensing apparatus according to claim 1, wherein the stopper comprises resilient material.

6. A fluid dispensing apparatus according to claim 4, wherein the stopper comprises a synthetic or naturally occurring polymeric material.

7. A fluid dispensing apparatus according to claim 6, wherein the stopper comprises an elastomeric material.

8. A fluid dispensing apparatus according to claim 7, wherein said elastomeric material is a Thermoplastic Elastomer (TPE) material.

9. A fluid dispensing apparatus according to claim 1, wherein the stopper comprises a material of hardness of from 30 to 40 Shore A.

10. A fluid dispensing apparatus according to claim 1, wherein in the first position the stopper experiences a compressive force such as to ensure sufficient sealing contact with the dispensing nozzle.

11. A fluid dispensing apparatus according to claim 10, wherein the compressive force experienced by the stopper is greater than 1.5N.

12. A fluid dispensing apparatus according to claim 1, wherein the end cap is formed as a moulding and the stopper insert is provided as a second moulding thereto.

13. A fluid dispensing apparatus according to claim 1, wherein the end cap is provided with one or more guide projections shaped for receipt by apertures and/or channels defined by the body to align the end cap with the body.

14. A fluid dispensing apparatus according to claim 13, wherein the one or more guide projections comprise retaining means for reversibly retaining the end cap to the body.

15. A fluid dispensing apparatus according to claim 1, wherein the end cap comprises a rigid material.

16. A fluid dispensing apparatus according to claim 1, wherein said reservoir contains a volume of fluid medicament formulation.

17. A fluid dispensing apparatus according to claim 1, wherein said fluid is a liquid, and wherein the protective end cap and stopper are adapted to seal the dispensing nozzle orifice to reduce drain back of liquid within the nozzle.

* * * * *